United States Patent
Kamon

(10) Patent No.: US 10,426,318 B2
(45) Date of Patent: Oct. 1, 2019

(54) IMAGE PROCESSING APPARATUS, ENDOSCOPE SYSTEM, AND IMAGE PROCESSING METHOD

(71) Applicant: FUJIFILM Corporation, Tokyo (JP)

(72) Inventor: Shumpei Kamon, Kanagawa (JP)

(73) Assignee: FUJIFILM, Tokyo (JP)

( * ) Notice: Subject to any disclaimer, the term of this patent is extended or adjusted under 35 U.S.C. 154(b) by 0 days.

(21) Appl. No.: 15/936,475

(22) Filed: Mar. 27, 2018

(65) Prior Publication Data
US 2018/0214004 A1 Aug. 2, 2018

Related U.S. Application Data

(63) Continuation of application No. PCT/JP2016/078816, filed on Sep. 29, 2016.

(30) Foreign Application Priority Data

Sep. 29, 2015 (JP) .................. 2015-192003

(51) Int. Cl.
*G06K 9/00* (2006.01)
*A61B 1/00* (2006.01)
(Continued)

(52) U.S. Cl.
CPC ............ *A61B 1/00009* (2013.01); *A61B 1/00* (2013.01); *A61B 1/04* (2013.01); *A61B 1/05* (2013.01);
(Continued)

(58) Field of Classification Search
CPC ....... A61B 1/00009; A61B 1/05; A61B 8/488; A61B 5/14552; A61B 5/02007; A61B 5/7264; G06T 7/0012; H04N 5/2256
See application file for complete search history.

(56) References Cited

U.S. PATENT DOCUMENTS 9,014,772 B2  4/2015  Yamaguchi et al.
9,044,163 B2  6/2015  Yamaguchi et al.
(Continued)

FOREIGN PATENT DOCUMENTS

EP    2505121     10/2012
JP    H07210655   8/1995
(Continued)

OTHER PUBLICATIONS

"Office Action of Japan Counterpart Application," with English translation thereof, dated Oct. 25, 2018, p. 1-p. 6.
(Continued)

*Primary Examiner* — Amir Alavi
(74) *Attorney, Agent, or Firm* — JCIPRNET

(57) ABSTRACT

There are provided an image processing apparatus, an endoscope system, and an image processing method for assisting diagnosis more effectively by calculating more intuitive and useful information than blood vessel information for a specific submucosal depth. An image processing apparatus includes a processor configured to function as an image acquisition unit that acquires an endoscope image, a blood vessel extraction unit that extracts a blood vessel at a specific depth of the observation target from the endoscope image, a blood vessel information calculation unit that calculates blood vessel information regarding the blood vessel extracted by the blood vessel extraction unit, and a blood vessel parameter calculation unit that calculates a blood vessel parameter, which is relevant to the blood vessel at the specific depth, by calculation using the blood vessel information.

17 Claims, 12 Drawing Sheets

(51) Int. Cl.
　　　A61B 1/04　　　(2006.01)
　　　A61B 5/107　　(2006.01)
　　　A61B 1/05　　　(2006.01)
　　　A61B 5/02　　　(2006.01)
　　　A61B 5/1455　　(2006.01)
　　　A61B 5/00　　　(2006.01)
　　　G06T 7/00　　　(2017.01)
　　　H04N 5/225　　(2006.01)
　　　A61B 1/06　　　(2006.01)
　　　A61B 8/08　　　(2006.01)

(52) U.S. Cl.
　　　CPC .......... *A61B 5/02007* (2013.01); *A61B 5/107* (2013.01); *A61B 5/14552* (2013.01); *A61B 5/7264* (2013.01); *G06T 7/0012* (2013.01); *H04N 5/2256* (2013.01); *A61B 1/041* (2013.01); *A61B 1/0684* (2013.01); *A61B 8/488* (2013.01); *G06T 2207/30101* (2013.01); *H04N 2005/2255* (2013.01)

(56) References Cited

U.S. PATENT DOCUMENTS

| 2010/0097454 | A1* | 4/2010 | Kubo | A61B 1/00188 |
| | | | | 348/65 |
| 2011/0112362 | A1 | 5/2011 | Minetoma | |
| 2011/0245642 | A1* | 10/2011 | Minetoma | A61B 1/0638 |
| | | | | 600/324 |
| 2014/0316195 | A1 | 10/2014 | Kaku et al. | |
| 2014/0316283 | A1 | 10/2014 | Kaku et al. | |
| 2015/0363932 | A1 | 12/2015 | Hirota et al. | |
| 2018/0206738 | A1* | 7/2018 | Kamon | G02B 23/24 |
| 2018/0214004 | A1* | 8/2018 | Kamon | A61B 1/00 |
| 2018/0218499 | A1* | 8/2018 | Kamon | A61B 1/00 |
| 2019/0008362 | A1* | 1/2019 | Kamon | A61B 1/00 |
| 2019/0021579 | A1* | 1/2019 | Kamon | A61B 1/00 |

FOREIGN PATENT DOCUMENTS

| JP | 2005157902 | 6/2005 |
| JP | 2007061638 | 3/2007 |
| JP | 2009207541 | 9/2009 |
| JP | 2011217798 | 11/2011 |
| JP | 2012125501 | 7/2012 |
| JP | 2012213550 | 11/2012 |
| JP | 2012213552 | 11/2012 |
| JP | 2013013559 | 1/2013 |
| WO | 2014132695 | 9/2014 |

OTHER PUBLICATIONS

"Search Report of Europe Counterpart Application", dated Oct. 2, 2018, p. 1-p. 8.

"International Search Report (Form PCT/ISA/210) of PCT/JP2016/078816", dated Nov. 8, 2016, with English translation thereof, pp. 1-5.

"International Preliminary Report on Patentability (Form PCT/IPEA/409)", published on Oct. 23, 2017, with English translation thereof, pp. 1-9.

Office Action of Japan Counterpart Application, with English translation thereof, dated Jun. 11, 2019, pp. 1-7.

* cited by examiner

IMAGE PROCESSING APPARATUS, ENDOSCOPE SYSTEM, AND IMAGE PROCESSING METHOD

CROSS-REFERENCE TO RELATED APPLICATIONS

This application is a Continuation of PCT International Application No. PCT/JP2016/078816 filed on 29 Sep. 2016, which claims priority under 35 U.S.C. § 119(a) to Japanese Patent Application No. 2015-192003 filed on 29 Sep. 2015. The above application is hereby expressly incorporated by reference, in its entirety, into the present application.

BACKGROUND OF THE INVENTION

1. Field of the Invention

The present invention relates to an image processing apparatus, an endoscope system, and an image processing method for calculating data, such as numerical values to be used for diagnosis, by using an endoscope image captured by an endoscope.

2. Description of the Related Art

In the medical field, diagnosis using an endoscope system including a light source device, an endoscope, and a processor device has been widely performed. In the diagnosis using the endoscope system, an insertion part of the endoscope is inserted into a subject, illumination light is emitted from the distal end portion, and an observation target irradiated with the illumination light (mucous membrane or the like inside the subject) is imaged by an imaging sensor mounted in the distal end portion of the endoscope. Then, an image (hereinafter, referred to as an endoscope image) of the observation target is generated using an image signal obtained by the imaging, and is displayed on the monitor.

Usually, in the endoscope system, an endoscope image in which the observation target can be observed with a natural color shade (hereinafter, referred to as a normal light image) is displayed by imaging the observation target irradiated with white illumination light (also referred to as normal light). In addition, an endoscope system that obtains an endoscope image (hereinafter, referred to as a special observation image) emphasizing a blood vessel, a pit pattern, and the like of the observation target by using light having a specific wavelength range as illumination light has also become widespread. In the case of performing diagnosis using an endoscope image, information of blood vessels, pit patterns, and the like is an important diagnostic material. Therefore, special observation images emphasizing these are particularly useful for diagnosis.

In recent years, an endoscope system or a diagnostic assistance apparatus is also known that assists a doctor's diagnosis by calculating the depth, thickness, density, and the like of blood vessels using an endoscope image (or an image signal used to generate an endoscope image) (JP2007-061638A and JP2011-217798A (corresponding to US2011/0245642A1)). In addition, an endoscope system is also known in which division into a surface layer, a middle layer, and a deep layer (or a surface layer and a middle deep layer) is performed according to the depth with the mucosal surface as a reference and the oxygen saturation at each of the layers is calculated (JP2012-125501A (corresponding to U.S. Pat. No. 9,044,163B2) and JP2012-213550A (corresponding to U.S. Pat. No. 9,014,772B2).

SUMMARY OF THE INVENTION

As in JP2007-061638A and JP2011-217798A, information regarding blood vessels that can be calculated using an endoscope image (hereinafter, referred to as blood vessel information) is useful information for diagnosis. However, a doctor does not perform diagnosis based on only one of the pieces of blood vessel information, such as the depth, thickness, density, and the like of blood vessels, but performs diagnosis by considering a plurality of pieces of blood vessel information in a complex manner. For example, the thickness of the blood vessel and the density of the blood vessel are useful blood vessel information for diagnosis. However, the state of the observation target is not determined just because the thickness of the blood vessel is a specific thickness or the density of the blood vessel is a specific density, but diagnosis is performed by taking into consideration a plurality of pieces of blood vessel information, such as a case where the thickness of the blood vessel is equal to or greater than a specific thickness and the density of the blood vessel is equal to or greater than a specific value and accordingly the state of the observation target is a specific lesion.

In accordance with the actual condition of the multifaceted and complex diagnosis described above, in recent years, an endoscope system or an image processing apparatus for analyzing an endoscope image is required to assist a doctor's diagnosis by calculating more intuitive and useful information or the like than the blood vessel information calculated in the above JP2007-061638A and JP2011-217798A.

In the endoscope image, pieces of information in the submucosal depth direction are superimposed. Accordingly, it is not easy to distinguish the pieces of information in the submucosal depth direction by the endoscope image. For example, it is left to the sensory determination of an experienced doctor to distinguish and grasp the state of a blood vessel located at the surface layer of the mucous membrane (hereinafter, referred to as a surface layer blood vessel) and the state of a blood vessel located at the middle deep layer of the mucous membrane (hereinafter, referred to as a middle deep layer blood vessel). Therefore, it is desirable that the endoscope system or the image processing apparatus for analyzing the endoscope image calculates information regarding the blood vessel distinctively for each submucosal depth to assist the diagnosis.

Regarding this point, the endoscope systems disclosed in JP2012-125501A and JP2012-213550A calculate the oxygen saturation for each submucosal depth. Accordingly, a higher diagnostic assistance effect than in the previous endoscope systems is obtained. However, the oxygen saturation is calculated by the endoscope systems disclosed in JP2012-125501A and JP2012-213550A for each submucosal depth, and the oxygen saturation is blood vessel information that requires consideration of other information. For this reason, it is still required to calculate more intuitive and useful information or the like to assist diagnosis.

It is an object of the present invention to provide an image processing apparatus, an endoscope system, and an image processing method for assisting diagnosis more effectively by calculating more intuitive and useful information than blood vessel information for a specific submucosal depth.

An image processing apparatus of the present invention comprises: an image acquisition unit that acquires an endoscope image obtained by imaging an observation target with an endoscope; a blood vessel extraction unit that extracts a blood vessel for each depth at a specific depth of the observation target from the endoscope image; a blood vessel information calculation unit that calculates blood vessel information for each depth regarding the blood vessel extracted by the blood vessel extraction unit; and a blood vessel parameter calculation unit that calculates a blood vessel parameter for each depth, which is relevant to the blood vessel at the specific depth, by calculation for each depth using the blood vessel information.

It is preferable that the blood vessel information is the number of blood vessels extracted by the blood vessel extraction unit, a thickness, a change in thickness, complexity of thickness change, a length, a change in length, the number of branches, a branching angle, a distance between branch points, the number of crossings, a depth, a height difference, an inclination, an area, a density, an interval, a contrast, a color, a color change, a degree of meandering, blood concentration, oxygen saturation, a proportion of arteries, a proportion of veins, concentration of administered coloring agent, a running pattern, or a blood flow rate.

It is preferable that the blood vessel parameter calculation unit calculates the blood vessel parameter of the specific depth using the blood vessel information calculated for the blood vessel at the specific depth.

It is preferable that the blood vessel parameter calculation unit calculates the blood vessel parameter of the specific depth using the blood vessel information calculated for blood vessels having depths other than the specific depth.

It is preferable that the blood vessel parameter calculation unit calculates the blood vessel parameter by weighting a plurality of pieces of the blood vessel information.

It is preferable that the blood vessel parameter calculation unit performs the weighting using a coefficient determined by machine learning.

It is preferable that the blood vessel information calculation unit calculates a statistic in a region of interest, which is set in a part or entirety of the endoscope image, as the blood vessel information.

It is preferable that the statistic is a maximum value, a minimum value, an average value, a median, or a mode.

It is preferable that, in a case of setting the region of interest in a part of the endoscope image, the blood vessel information calculation unit calculates the blood vessel information of the region of interest and also calculates the blood vessel information for a region other than the region of interest and that the blood vessel parameter calculation unit calculates the blood vessel parameter using the blood vessel information of the region of interest and the blood vessel information of the region other than the region of interest.

It is preferable to further comprise a determination unit that determines a state of a mucous membrane of the observation target using the blood vessel parameter.

It is preferable that the determination unit determines the state of the mucous membrane of the observation target according to a change of the blood vessel parameter with respect to a depth.

It is preferable that the determination unit determines the state of the mucous membrane of the observation target using a plurality of the blood vessel parameters.

It is desirable that the determination unit determines the state of the mucous membrane of the observation target to be one of three or more kinds of states including normal, adenoma, and cancer using the blood vessel parameter.

It is desirable that the determination unit determines the state of the mucous membrane of the observation target to be one of normal, hyperplastic polyp, SSA/P, adenoma, laterally spreading tumor, and cancer using the blood vessel parameter.

It is preferable that the determination unit determines a stage of cancer using the blood vessel information or the blood vessel parameter in a case where the state of the mucous membrane of the observation target is cancer.

An endoscope system of the present invention comprises: an endoscope that images an observation target; and an image processing apparatus having an image acquisition unit that acquires an endoscope image obtained by imaging the observation target with the endoscope, a blood vessel extraction unit that extracts a blood vessel for each depth at a specific depth of the observation target from the endoscope image, a blood vessel information calculation unit that calculates blood vessel information for each depth regarding the blood vessel extracted by the blood vessel extraction unit, and a blood vessel parameter calculation unit that calculates a blood vessel parameter for each depth, which is relevant to the blood vessel at the specific depth, by calculation for each depth using the blood vessel information.

An image processing method of the present invention includes: a step in which an image acquisition unit acquires an endoscope image obtained by imaging an observation target with an endoscope; a step in which a blood vessel extraction unit extracts a blood vessel for each depth at a specific depth of the observation target from the endoscope image; a step in which a blood vessel information calculation unit calculates blood vessel information for each depth regarding the blood vessel extracted by the blood vessel extraction unit; and a step in which a blood vessel parameter calculation unit calculates a blood vessel parameter for each depth, which is relevant to the blood vessel at the specific depth, by calculation for each depth using a plurality of pieces of the blood vessel information.

Since the image processing apparatus, the endoscope system, and the image processing method of the present invention calculate more intuitive and useful blood vessel parameters than blood vessel information for a specific submucosal depth, it is possible to assist the doctor's diagnosis more directly and effectively than in the related art.

DESCRIPTION OF THE PREFERRED EMBODIMENTS

First Embodiment

Figure 1:
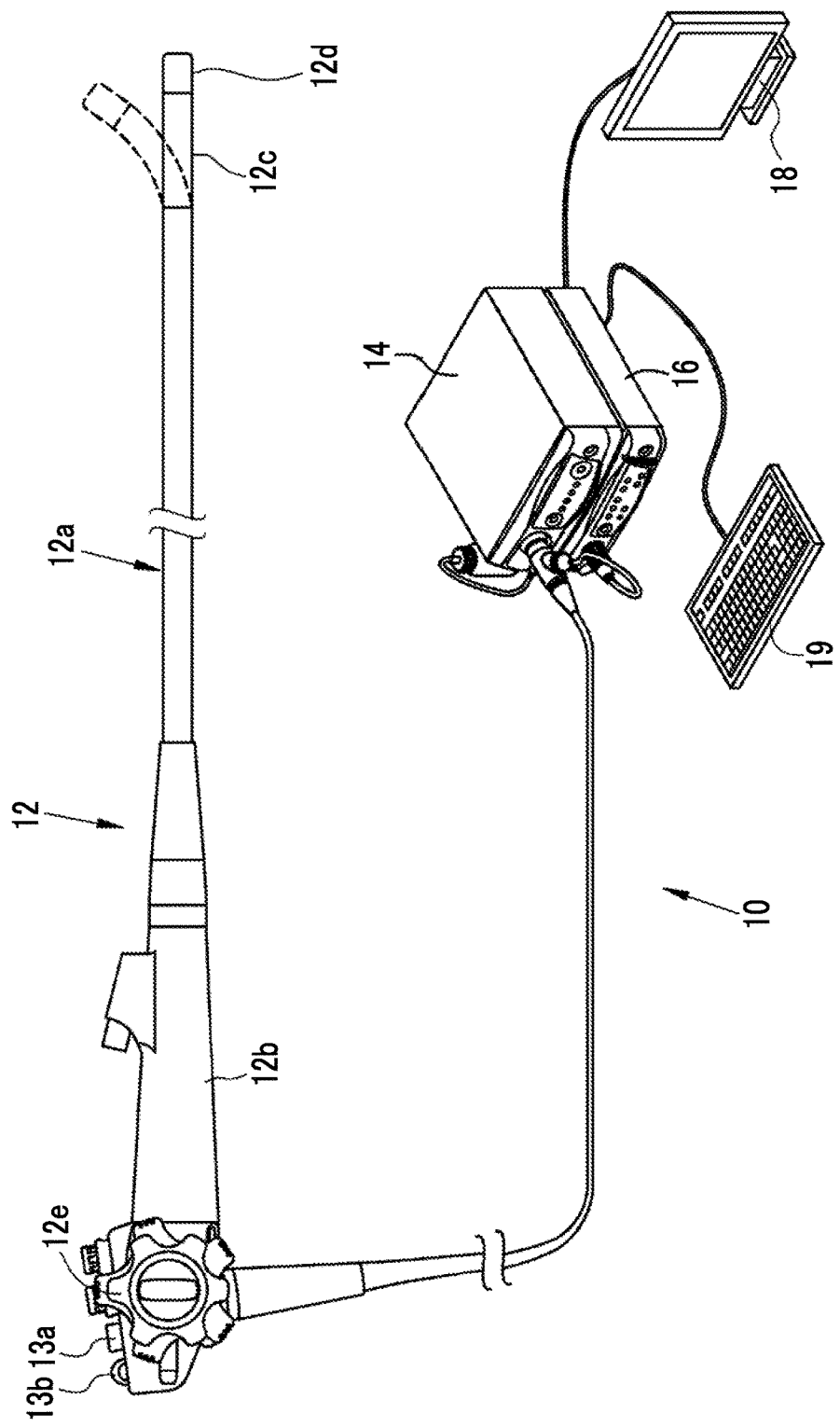
FIG. 1 is an external view of an endoscope system.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is inserted into a subject, an operation unit 12b provided in a proximal end portion of the insertion part 12a, and a bending portion 12c and a distal end portion 12d that are provided on the distal end side of the insertion part 12a. By operating an angle knob 12e of the operation unit 12b, the bending portion 12c is bent. Through the bending operation, the distal end portion 12d is directed in a desired direction.

In addition to the angle knob 12e, a still image acquisition instruction unit 13a and a zoom operation unit 13b are provided in the operation unit 12b. The still image acquisition instruction unit 13a operates in the case of inputting a still image acquisition instruction to the endoscope system 10. The instruction to acquire a still image includes a freeze instruction for displaying a still image of an observation target on the monitor 18 and a release instruction for storing a still image in a storage. The zoom operation unit 13b is used to input an imaging magnification change instruction for changing the imaging magnification.

The processor device 16 is electrically connected to the monitor 18 and the console 19. The monitor 18 outputs and displays an image of the observation target, information attached to the image, and the like. The console 19 functions as a user interface for receiving an input operation, such as a function setting.

Figure 2:
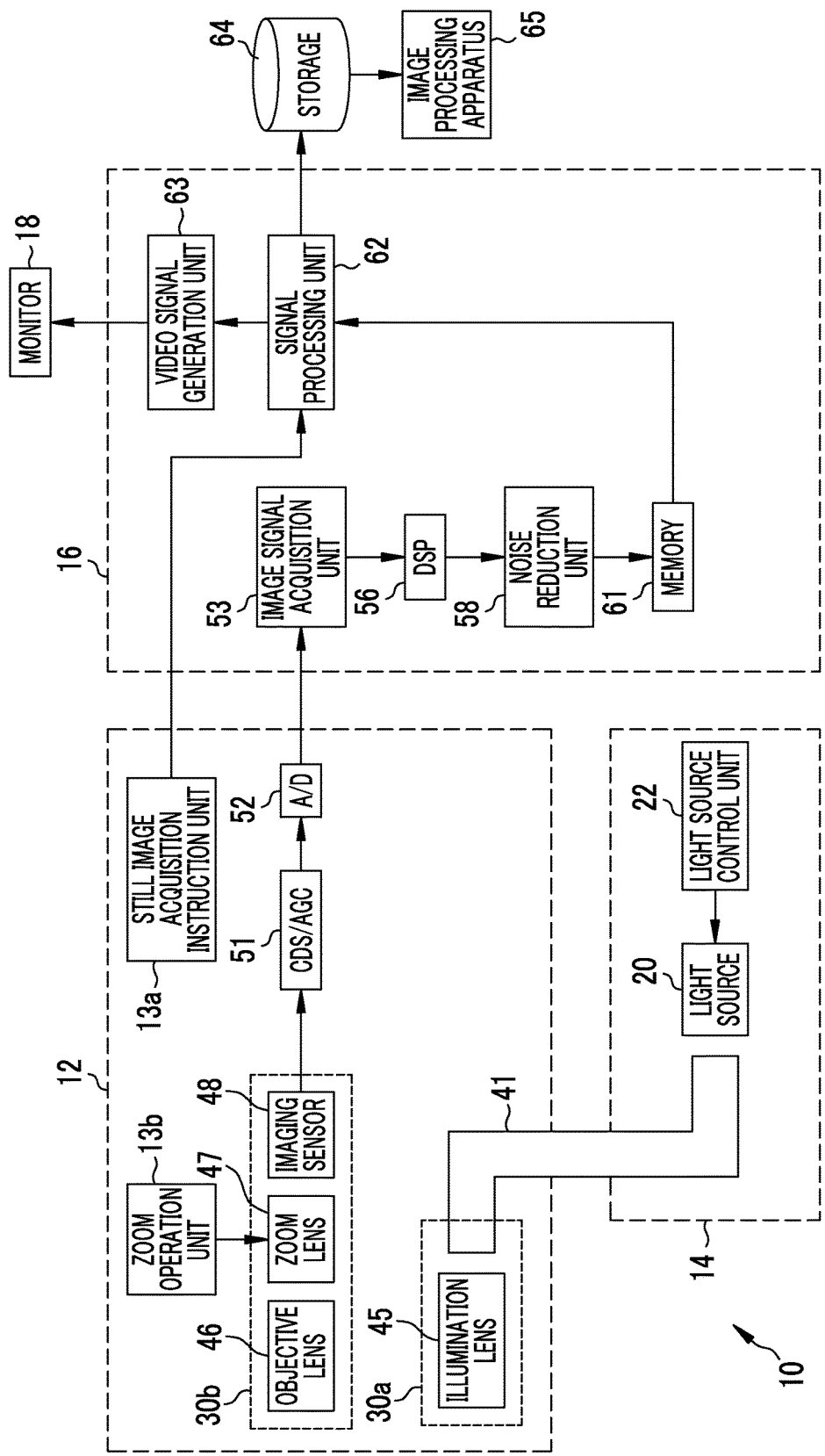
FIG. 2 is a block diagram of the endoscope system.

As shown in FIG. 2, the light source device 14 includes a light source 20 that emits illumination light to be emitted to the observation target and a light source control unit 22 that controls the light source 20. The light source 20 is, for example, a semiconductor light source such as a light emitting diode (LED) of a plurality of colors, a combination of a laser diode and a phosphor, or a halogen light source such as a xenon lamp. The light source 20 includes an optical filter for adjusting the wavelength range of light emitted from the LED or the like. The light source control unit 22 controls the amount of illumination light by ON/OFF of the LED or the like or by adjusting the driving current or the driving voltage of the LED or the like. In addition, the light source control unit 22 controls the wavelength range of illumination light by changing the optical filter or the like.

The endoscope system 10 has two types of observation modes, that is, a normal observation mode for observing an observation target in a normal observation image and a special observation mode for observing an observation target in a special observation image. In a case where the observation mode is a normal observation mode, the light source control unit 22 causes the light source 20 to generate approximately white illumination light. In a case where the observation mode is a special observation mode, the light source control unit 22 causes the light source 20 to generate illumination light having a specific narrow wavelength range (hereinafter, referred to as narrowband light). The observation mode is switched by a mode change switch (not shown) provided in the operation unit 12b.

The light source 20 can generate a plurality of kinds of narrowband light, such as violet narrowband light having a center wavelength (or a peak wavelength at which spectral intensity is maximized; the same hereinbelow) in a violet wavelength range (wavelength range of about 350 to 400 nm), blue narrowband light having a center wavelength in a blue wavelength range (wavelength range of about 400 to 500 nm), green narrowband light having a center wavelength in a green wavelength range (wavelength range of about 500 to 600 nm), and red narrowband light having a center wavelength in a red wavelength range (wavelength range of about 600 to 750 nm). More specifically, the light source 20 can generate violet narrowband light having a center wavelength of about 400±10 nm, blue narrowband light having a center wavelength of about 450±10 nm, blue narrowband light having a center wavelength of about 470±10 nm, and the like. Since the center wavelength of each narrowband light can be designated by changing an optical filter or the like, two or more blue narrowband light beams having different center wavelengths can be generated as described above. This also applies to violet narrowband light, green narrowband light, and red narrowband light.

In the special observation mode, the light source 20 generates at least two or more kinds of narrowband light beams having different center wavelengths among the plurality of kinds of narrowband light beams, and images the observation target irradiated with each of the narrowband light beams. Therefore, in the special observation mode, a plurality of kinds of endoscope images corresponding to the kinds of narrowband light beams are obtained. In the present embodiment, in the case of the special observation mode, the light source 20 alternately generates two kinds of narrowband light beams of first narrowband light (for example, violet narrowband light) and second narrowband light (for example, blue narrowband light having a center wavelength of about 450±10 nm) whose center wavelength or peak wavelength is in a longer wavelength range than the first narrowband light.

The illumination light emitted from the light source 20 is incident on a light guide 41 inserted into the insertion part 12a. The light guide 41 is built into the endoscope 12 and a universal cord, and propagates the illumination light to the distal end portion 12d of the endoscope 12. The universal cord is a cord for connecting the endoscope 12 with the light source device 14 and the processor device 16. As the light guide 41, it is possible to use a multi-mode fiber. As an example, it is possible to use a small-diameter fiber cable having a diameter of ϕ0.3 mm to ϕ0.5 mm that includes a core with a diameter of 105 μm, a cladding with a diameter of 125 μm, and a protective layer as an outer skin.

An illumination optical system 30a and an imaging optical system 30b are provided in the distal end portion 12d of the endoscope 12. The illumination optical system 30a has an illumination lens 45, and the illumination light propagated by the light guide 41 is emitted to the observation target through the illumination lens 45. The imaging optical system 30b has an objective lens 46, a zoom lens 47, and an imaging sensor 48. Various kinds of light, such as reflected light, scattered light, and fluorescence from the observation target, are incident on the imaging sensor 48 through the objective lens 46 and the zoom lens 47. As a result, an image of the observation target is formed on the imaging sensor 48. The zoom lens 47 is moved freely between the telephoto end and the wide end by operating the zoom operation unit 13*b*, thereby enlarging or reducing the observation target formed on the imaging sensor 48.

The imaging sensor 48 is a color imaging sensor in which any one of red (R), green (G), and blue (B) color filters is provided for each pixel, and images the observation target and outputs the image signals of the respective colors of RGB. As the imaging sensor 48, it is possible to use a charge coupled device (CCD) imaging sensor or a complementary metal oxide semiconductor (CMOS) imaging sensor. Instead of the imaging sensor 48 in which primary color filters are provided, a complementary color imaging sensor including complementary color filters of cyan (C), magenta (M), yellow (Y), and green (G) may be used. In a case where a complementary color imaging sensor is used, image signals of four colors of CMYG are output. Therefore, by converting the image signals of four colors of CMYG into image signals of three colors of RGB by complementary color-primary color conversion, it is possible to obtain the same RGB image signals as in the imaging sensor 48. Instead of the imaging sensor 48, a monochrome sensor in which no color filter is provided may be used.

The image signal output from the imaging sensor 48 is transmitted to a CDS/AGC circuit 51. The CDS/AGC circuit 51 performs correlated double sampling (CDS) or automatic gain control (AGC) for the image signal that is an analog signal. The image signal transmitted through the CDS/AGC circuit 51 is converted into a digital image signal by an analog to digital (A/D) converter 52. The digital image signal after A/D conversion is input to the processor device 16.

The processor device 16 includes an image signal acquisition unit 53, a digital signal processor (DSP) 56, a noise reduction unit 58, a memory 61, a signal processing unit 62, and a video signal generation unit 63.

The image signal acquisition unit 53 acquires a digital image signal from the endoscope 12. The DSP 56 performs various kinds of signal processing, such as defect correction processing, offset processing, gain correction processing, linear matrix processing, gamma conversion processing, and demosaic processing, on the image signal acquired by the image signal acquisition unit 53. In the defect correction processing, the signal of a defective pixel of the imaging sensor 48 is corrected. In the offset processing, a dark current component is removed from the image signal subjected to the defect correction processing, and an accurate zero level is set. In the gain correction processing, the signal level is adjusted by multiplying the image signal after the offset processing by a specific gain.

Linear matrix processing for increasing color reproducibility is performed on the image signal after the gain correction processing. Then, the brightness or saturation is adjusted by gamma conversion processing. Demosaic processing (also referred to as isotropic processing or synchronization processing) is performed on the image signal after the gamma conversion processing, and the signal of missing color in each pixel is generated by interpolation. Through the demosaic processing, all pixels have signals of RGB colors. The noise reduction unit 58 reduces noise by performing noise reduction processing on the image signal subjected to the demosaic processing or the like by the DSP 56 using, for example, a moving average method or a median filter method. The image signal from which noise has been reduced is stored in the memory 61.

The signal processing unit 62 acquires the image signal after noise reduction from the memory 61. Then, image processing, such as color conversion processing, color emphasis processing, and structure emphasis processing, is performed on the acquired image signal as necessary, thereby generating a color endoscope image in which the observation target is reflected. The color conversion processing is a process of performing color conversion on the image signal by 3×3 matrix processing, gradation conversion processing, three-dimensional look-up table (LUT) processing, and the like. The color emphasis processing is performed on the image signal after the color conversion processing. The structure emphasis processing is a process of emphasizing a specific tissue or structure included in an observation target, such as a blood vessel or a pit pattern, and is performed on the image signal after the color emphasis processing. Since the endoscope image generated by the signal processing unit 62 is a normal observation image in a case where the observation mode is a normal observation mode and is a special observation image in a case where the observation mode is a special observation mode, the content of the color conversion processing, the color emphasis processing, and the structure emphasis processing differs depending on the observation mode. In the case of the normal observation mode, the signal processing unit 62 generates a normal observation image by performing the above-described various kinds of signal processing by which the observation target has a natural color shade. In the case of the special observation mode, the signal processing unit 62 generates a special observation image by performing the above-described various kinds of signal processing for emphasizing at least a blood vessel of the observation target. In the special observation image generated by the signal processing unit 62, a blood vessel (so-called surface layer blood vessel) located at a relatively shallow position inside the observation target with the surface of the mucous membrane as a reference has a magenta type color (for example, brown color), and a blood vessel located at a relatively deep position inside the observation target with the surface of the mucous membrane as a reference (so-called middle deep layer blood vessel) has a cyan type color (for example, green color). For this reason, the blood vessel of the observation target is emphasized due to the color difference with respect to the mucous membrane expressed by a pink type color.

Figure 3:
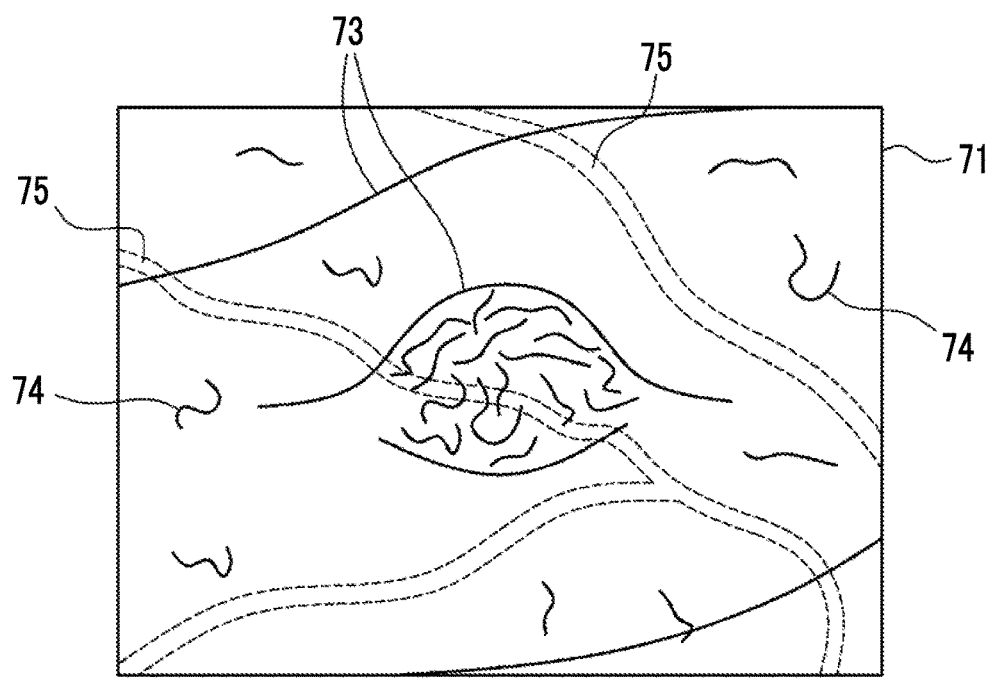
FIG. 3 is a first endoscope image.
Figure 4:
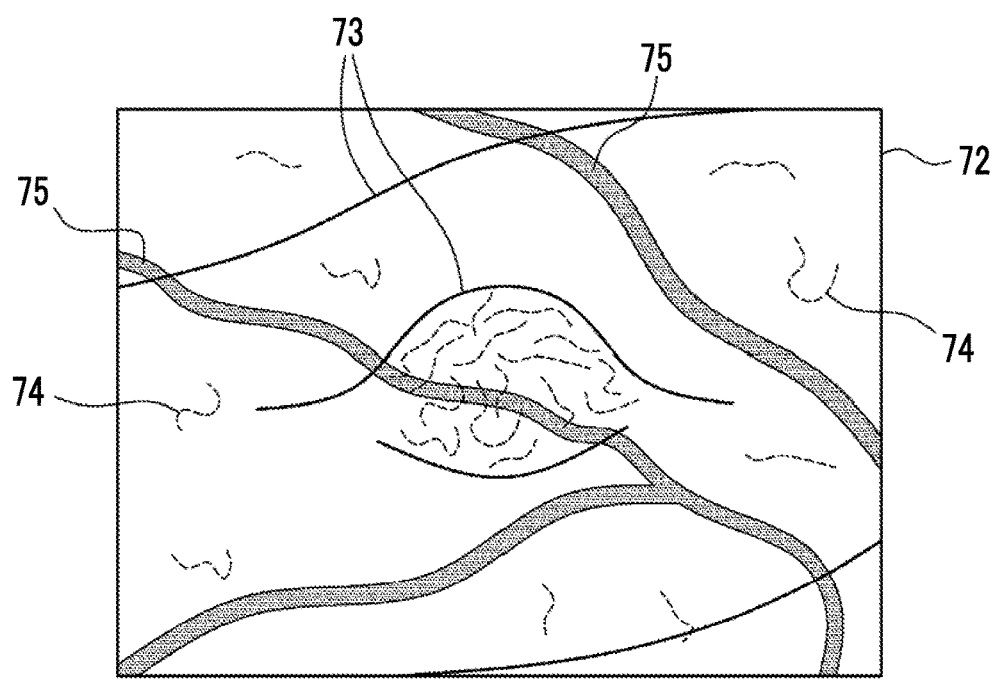
FIG. 4 is a second endoscope image.

In the special observation mode of the present embodiment, the light source 20 generates two kinds of narrowband light beams of the first narrowband light and the second narrowband light. Therefore, an endoscope image (hereinafter, referred to as a first endoscope image) 71 shown in FIG. 3, which is obtained by imaging the observation target irradiated with the first narrowband light, and an endoscope image (hereinafter, referred to as a second endoscope image) 72 shown in FIG. 4, which is obtained by imaging the observation target irradiated with the second narrowband light, are obtained. In the first endoscope image 71 and the second endoscope image 72, not only can the shape 73 of the mucosal surface of the observation target be observed, but also a thin surface layer blood vessel 74 located relatively close to the mucosal surface is expressed by a magenta type color and a thick middle deep layer blood vessel 75 located at a relatively deep position under the mucous membrane is expressed by a cyan type color so as to be emphasized. However, the first narrowband light and the second narrowband light have different center wavelengths, and the center wavelength of the first narrowband light is shorter than the center wavelength of the second narrowband light. Therefore, depending on the difference in the degree of penetration of the first narrowband light and the second narrowband light into the submucous membrane, the appearance of blood vessels differs between the first endoscope image 71 and the second endoscope image 72. For example, the surface layer blood vessel 74 can be more clearly observed in the first endoscope image 71 than in the second endoscope image 72, but the middle deep layer blood vessel 75 can be more clearly observed in the second endoscope image 72 than in the first endoscope image 71.

The signal processing unit 62 inputs the generated endoscope image to the video signal generation unit 63. The video signal generation unit 63 converts the endoscope image into a video signal to be output and displayed on the monitor 18. In a case where a release instruction is input by operating the still image acquisition instruction unit 13a, the signal processing unit 62 stores the generated endoscope image in a storage 64. The storage 64 is an external storage device connected to the processor device 16 through a local area network (LAN). For example, the storage 64 is a file server of a system for filing an endoscope image, such as a picture archiving and communication system (PACS), or a network attached storage (NAS). The endoscope image stored in the storage 64 is used by an image processing apparatus 65.

Figure 5:
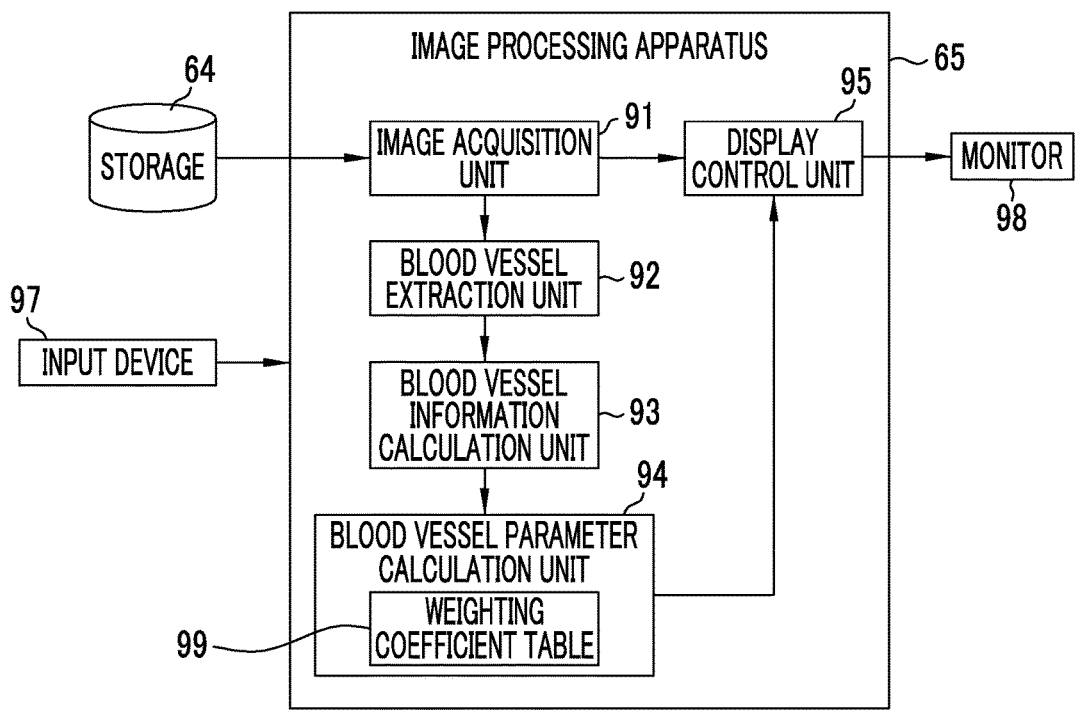
FIG. 5 is a block diagram of an image processing apparatus.

The image processing apparatus 65 is an apparatus that performs image processing on the endoscope image to calculate a blood vessel parameter for diagnostic assistance. As shown in FIG. 5, the image processing apparatus 65 includes an image acquisition unit 91, a blood vessel extraction unit 92, a blood vessel information calculation unit 93, a blood vessel parameter calculation unit 94, and a display control unit 95. An input device 97 including a keyboard and a pointing device used for designating a region of interest (ROI) or a monitor 98 for displaying an endoscope image and the like is connected to the image processing apparatus 65.

The image acquisition unit 91 acquires an endoscope image captured by the endoscope 12 (including a case of an image signal that becomes a basis of the endoscope image) from the storage 64. Endoscope images stored in the storage 64 include a normal observation image and a special observation image. In the present embodiment, the image acquisition unit 91 acquires a first endoscope image 71 and a second endoscope image 72, which are special observation images, from the storage 64.

The blood vessel extraction unit 92 extracts blood vessels within a specific depth range of the observation target (hereinafter, referred to as a specific depth) using the endoscope image acquired by the image acquisition unit 91. In the present embodiment, the reference of depth is a mucosal surface. The depth may be defined with an arbitrary portion (for example, muscularis mucosa) other than the mucosal surface as a reference. In addition, with a blood vessel at an arbitrary depth as a reference, the depth of other blood vessels may be defined as a relative depth from the blood vessel at the arbitrary depth.

Figure 6:
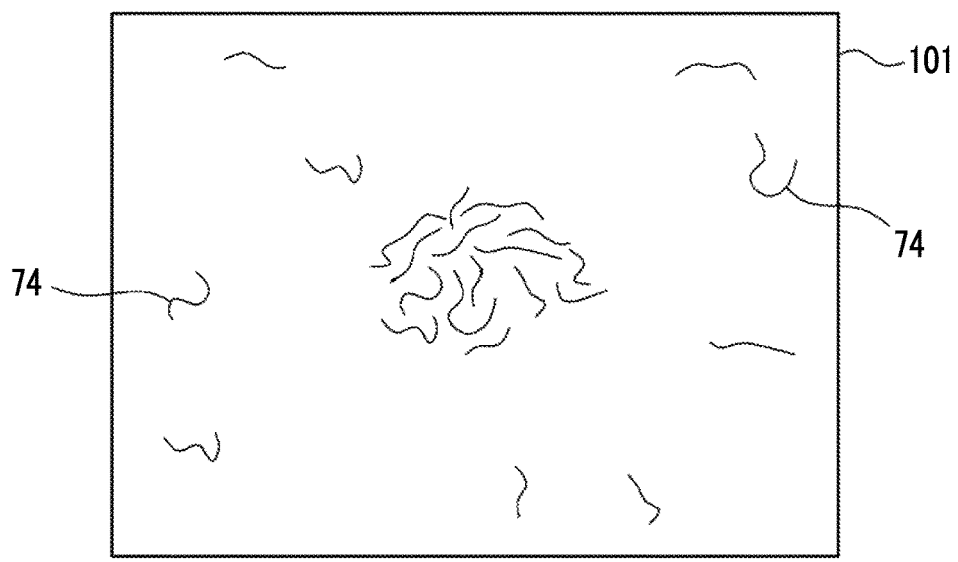
FIG. 6 is a difference image obtained by extracting a surface layer blood vessel.

In the present embodiment, the blood vessel extraction unit 92 extracts blood vessels at a specific depth by calculating the difference between the first endoscope image 71 and the second endoscope image 72. For example, by multiplying the first endoscope image 71 and the second endoscope image 72 by an appropriate number and subtracting the second endoscope image 72 from the first endoscope image 71, it is possible to extract the surface layer blood vessel 74 as in a difference image 101 shown in FIG. 6. That is, the difference image 101 is an image obtained by extracting only the surface layer blood vessel 74 at a specific depth of "surface layer" from the surface layer blood vessel 74 and the middle deep layer blood vessel 75 appearing in the original first endoscope image 71 and second endoscope image 72.

Figure 7:
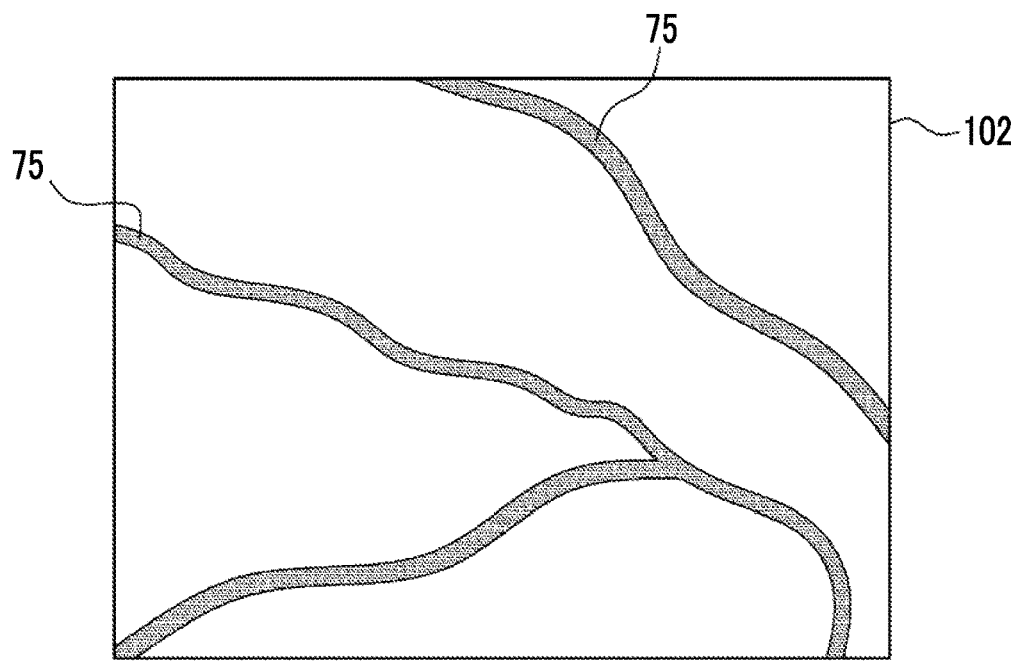
FIG. 7 is a difference image obtained by extracting a middle deep layer blood vessel.

Similarly, by multiplying the first endoscope image 71 and the second endoscope image 72 by an appropriate number and subtracting the first endoscope image 71 from the second endoscope image 72, it is possible to extract the middle deep layer blood vessel 75 as in a difference image 102 shown in FIG. 7. The difference image 102 is an image obtained by extracting only the middle deep layer blood vessel 75 having a submucosal depth of a specific depth called "middle deep layer" from the surface layer blood vessel 74 and the middle deep layer blood vessel 75 appearing in the original first endoscope image 71 and second endoscope image 72.

For example, the "surface layer" means that the depth from the mucosal surface is in the range of about 0 to 50 μm, the "middle layer" means that the depth from the mucosal surface is in the range of about 50 to 200 μm, and the "deep layer" means that the depth from the mucosal surface is in the range of about 200 to 500 μm. The "middle deep layer" is a combined range of the middle layer and the deep layer, and the depth from the mucosal surface is in the range of about 50 to 200 μm. Needless to say, the depth range of each of these layers is an example. The depth from the mucosal surface can be classified in a different way other than three layers (surface layer, middle layer, and deep layer) or two layers (surface layer and middle deep layer). That is, the depth from the mucosal surface may be classified into four or more layers. In the present embodiment, for the sake of simplicity, the depth from the mucosal surface is classified into two layers of "surface layer" and "middle deep layer". Therefore, in the present embodiment, the "specific depth" is "surface layer" or "middle deep layer".

In the present embodiment, as described above, the blood vessel extraction unit 92 extracts blood vessels at a specific depth by calculating the difference between the first endoscope image 71 and the second endoscope image 72. However, it is also possible to extract the surface layer blood vessel 74 or the middle deep layer blood vessel 75 using other extraction methods. For example, the surface layer blood vessel 74 or the middle deep layer blood vessel 75 can also be extracted by performing frequency filtering on the first endoscope image 71 or the second endoscope image 72.

The blood vessel information calculation unit 93 calculates blood vessel information regarding the blood vessel extracted by the blood vessel extraction unit 92. The blood vessel information is, for example, the number of blood vessels, the number of branches, a branching angle, a distance between branch points, the number of crossings, a thickness, a change in thickness, complexity of thickness change, a length, an interval, a depth, a height difference, an inclination, an area, a density, a contrast, a color, color change, degree of meandering, blood concentration, oxygen saturation, proportion of arteries, proportion of veins, concentration of administered coloring agent, a running pattern, or a blood flow rate. In the present embodiment, the blood vessel information calculation unit 93 calculates at least two or more kinds of blood vessel information among the pieces of blood vessel information.

The number of blood vessels is the number of blood vessels extracted in the entire endoscope image or in a region of interest. The number of blood vessels is calculated using, for example, the number of branch points (the number of branches) of the extracted blood vessel, the number of intersections (the number of crossings) with other blood vessels, and the like. The branching angle of a blood vessel is an angle formed by two blood vessels at a branch point. The distance between branch points is a linear distance between an arbitrary branch point and a branch point adjacent thereto or a length along a blood vessel from an arbitrary branch point to a branch point adjacent thereto.

The number of crossings between blood vessels is the number of intersections at which blood vessels having different submucosal depths cross each other on the endoscope image. More specifically, the number of crossings between blood vessels is the number of blood vessels, which are located at relatively shallow submucosal positions, crossing blood vessels located at deep positions.

The thickness of a blood vessel (blood vessel diameter) is a distance between the blood vessel and the boundary of the mucous membrane. For example, the thickness of a blood vessel (blood vessel diameter) is measured by counting the number of pixels along the lateral direction of the blood vessel from the edge of the extracted blood vessel through the blood vessel. Therefore, the thickness of a blood vessel is the number of pixels. However, in a case where the imaging distance, zoom magnification and the like at the time of capturing an endoscope image are known, the number of pixels can be converted into a unit of length, such as "µm", as necessary.

The change in the thickness of a blood vessel is blood vessel information regarding a variation in the thickness of the blood vessel, and is also referred to as the aperture inconsistency. The change in the thickness of a blood vessel is, for example, a change rate of the blood vessel diameter (also referred to as the degree of expansion). Using the thickness (minimum diameter) of the thinnest portion of the blood vessel and the thickness (maximum diameter) of the thickest portion of the blood vessel, the change rate of the blood vessel diameter is calculated as "blood vessel diameter change rate (%)=minimum diameter/maximum diameter×100".

In a case where an endoscope image obtained by imaging the observation target in a past examination and an endoscope image obtained by imaging the same observation target in a subsequent new examination are used, a temporal change in the thickness of the same blood vessel extracted from the endoscope image obtained by the subsequent new examination with respect to the thickness of the blood vessel extracted from the endoscope image obtained by the past examination may be the change in the thickness of the blood vessel.

As a change in the thickness of the blood vessel, a proportion of a small diameter portion or a proportion of a large diameter portion may be calculated. The small diameter portion is a portion whose thickness is equal to or less than the threshold value, and the large diameter portion is a portion where the thickness is equal to or greater than the threshold value. The proportion of a small diameter portion is calculated as "proportion of small diameter portion (%)=length of small diameter portion/length of blood vessel×100". Similarly, the proportion of a large diameter portion is calculated as "proportion of large diameter portion (%)=length of large diameter portion/length of blood vessel×100".

The complexity of the change in the thickness of a blood vessel (hereinafter, referred to as the "complexity of the thickness change") is blood vessel information indicating how complex the change is in a case where the thickness of the blood vessel changes, and is blood vessel information calculated by combining a plurality of pieces of blood vessel information indicating the change in the thickness of the blood vessel (that is, the change rate of the blood vessel diameter, the proportion of the small diameter portion, or the proportion of the large diameter portion). The complexity of the thickness change can be calculated, for example, by the product of the change rate of the blood vessel diameter and the proportion of the small diameter portion.

The length of a blood vessel is the number of pixels counted along the longitudinal direction of the extracted blood vessel.

The interval between blood vessels is the number of pixels showing the mucous membrane between the edges of the extracted blood vessel. In the case of one extracted blood vessel, the interval between blood vessels has no value.

The depth of a blood vessel is measured with the mucous membrane (more specifically, the mucosal surface) as a reference, for example. The depth of the blood vessel can be calculated based on, for example, the color of the blood vessel. In the case of the special observation image, a blood vessel located near the surface of the mucous membrane is expressed by a magenta type color, and a blood vessel far from the surface of the mucous membrane and located at a deep submucosal position is expressed by a cyan type color. Therefore, the blood vessel information calculation unit 93 calculates the depth of the blood vessel for each pixel based on the balance of the signals of the respective colors of R, G, and B of the pixels extracted as a blood vessel. In the present embodiment, the blood vessel extraction unit 92 extracts the surface layer blood vessel 74 or the middle deep layer blood vessel 75. However, the surface layer or the middle deep layer has a width. Therefore, as the depth of the blood vessel calculated by the blood vessel information calculation unit 93, the depth of a blood vessel within the range of "specific depth" is calculated. For example, since the middle deep layer blood vessel 75 is a blood vessel having a depth from the mucosal surface in a range of about 50 µm to 200 µm, the depth of the blood vessel calculated by the blood vessel information calculation unit 93 is a value within this range.

The height difference of a blood vessel is the magnitude of the difference in the depth of the blood vessel. For example, the height difference of one blood vessel of interest is calculated by the difference between the depth (maximum depth) of the deepest portion of the blood vessel and the depth (minimum depth) of the shallowest portion. In a case where the depth is constant, the height difference is zero. Similarly to the depth of the blood vessel, the change in the depth of the blood vessel or the height difference of the blood vessel is also a value within the range included in the "specific depth" to which the extracted blood vessel belongs.

The inclination of a blood vessel is the change rate of the depth of the blood vessel, and is calculated using the length of the blood vessel and the depth of the blood vessel. That is, the inclination of a blood vessel is calculated as "inclination of blood vessel=depth of blood vessel/length of blood vessel". The blood vessel may be divided into a plurality of sections, and the inclination of the blood vessel may be calculated in each section.

The area of a blood vessel is the number of pixels extracted as a blood vessel or a value proportional to the number of pixels extracted as a blood vessel. The area of a blood vessel is calculated within the region of interest, outside the region of interest, or for the entire endoscope image.

The density of blood vessels is a proportion of blood vessels in a unit area. A region of a specific size (for example, a region of a unit area) including pixels for calculating the density of blood vessels at its approximate center is cut out, and the proportion of blood vessels occupying all the pixels within the region is calculated. By performing this on all the pixels of the region of interest or the entire endoscope image, the density of blood vessels of each pixel can be calculated.

The contrast of a blood vessel is a relative contrast with respect to the mucous membrane of the observation target. The contrast of a blood vessel is calculated as, for example, "$Y_V/Y_M$" or "$(Y_V-Y_M)/(Y_V+Y_M)$", using the brightness $Y_V$ of the blood vessel and the brightness $Y_M$ of the mucous membrane.

The color of a blood vessel is each value of RGB of pixels showing the blood vessel. The change in the color of a blood vessel is a difference or ratio between the maximum value and the minimum value of the RGB values of pixels showing the blood vessel. For example, the ratio between the maximum value and the minimum value of the B value of a pixel showing the blood vessel, the ratio between the maximum value and the minimum value of the G value of a pixel showing the blood vessel, or the ratio between the maximum value and the minimum value of the R value of a pixel showing the blood vessel indicates a change in the color of the blood vessel. Needless to say, conversion into complementary colors may be performed to calculate the color of the blood vessel and a change in the color of the blood vessel for each value of cyan, magenta, yellow, green, and the like.

The degree of meandering of a blood vessel is blood vessel information indicating the size of a range in which the blood vessel travels meandering. The degree of meandering of a blood vessel is, for example, the area (the number of pixels) of a minimum rectangle including the blood vessel for which the degree of meandering is to be calculated. The ratio of the length of the blood vessel to the linear distance between the start point and the end point of the blood vessel may be used as the degree of meandering of the blood vessel.

The blood concentration of a blood vessel is blood vessel information proportional to the amount of hemoglobin contained in a blood vessel. Since the ratio (G/R) of the G value to the R value of a pixel showing a blood vessel is proportional to the amount of hemoglobin, the blood concentration can be calculated for each pixel by calculating the value of G/R.

The oxygen saturation of a blood vessel is the amount of oxygenated hemoglobin to the total amount of hemoglobin (total amount of oxygenated hemoglobin and reduced hemoglobin). The oxygen saturation can be calculated by using an endoscope image obtained by imaging the observation target with light in a specific wavelength range (for example, blue light having a wavelength of about 470±10 nm) having a large difference between the light absorption coefficients of oxygenated hemoglobin and reduced hemoglobin. In a case where blue light having a wavelength of about 470±10 nm is used, the B value of the pixel showing the blood vessel is correlated with the oxygen saturation. Therefore, by using a table or the like that associates the B value with the oxygen saturation, it is possible to calculate the oxygen saturation of each pixel showing the blood vessel.

The proportion of arteries is the ratio of the number of pixels of arteries to the number of pixels of all the blood vessels. Similarly, the proportion of veins is the ratio of the number of pixels of veins to the number of pixels of all the blood vessels. Arteries and veins can be distinguished by oxygen saturation. For example, assuming that a blood vessel having an oxygen saturation of 70% or more is an artery and a blood vessel having an oxygen saturation less than 70% is a vein, extracted blood vessels can be divided into arteries and veins. Therefore, the proportion of arteries and the proportion of veins can be calculated.

The concentration of an administered coloring agent is the concentration of a coloring agent sprayed on the observation target or the concentration of a coloring agent injected into the blood vessel by intravenous injection. The concentration of the administered coloring agent is calculated, for example, by the ratio of the pixel value of the coloring agent color to the pixel value of a pixel other than the coloring agent color. For example, in a case where a coloring agent for coloring in blue is administered, B/G, B/R, and the like indicate the concentration of the coloring agent fixed (or temporarily adhered) to the observation target.

The traveling pattern of a blood vessel is blood vessel information regarding the traveling direction of a blood vessel. The traveling pattern of a blood vessel is, for example, an average angle (traveling direction) of a blood vessel with respect to a reference line arbitrarily set, a dispersion (variation in traveling direction) of an angle formed by a blood vessel with respect to a reference line set arbitrarily, and the like.

The blood flow rate (also referred to as a blood flow speed) of a blood vessel is the number of red blood cells that can pass per unit time. In a case where an ultrasound probe is used together through the forceps channel of the endoscope 12 or the like, the Doppler shift frequency of each pixel showing the blood vessel of the endoscope image can be calculated by using the signal obtained by the ultrasound probe. The blood flow rate of the blood vessel can be calculated by using the Doppler shift frequency.

By operating the input device 97, it is possible to set a region of interest in a part or the entirety of the endoscope image. For example, in a case where a part of the endoscope image is set as a region of interest, the blood vessel information calculation unit 93 calculates blood vessel information within the region of interest. In a case where a region of interest is not designated or a case where the entire endoscope image is set as a region of interest, the blood vessel information calculation unit 93 calculates blood vessel information by setting the entire endoscope image as a region of interest.

The blood vessel information calculation unit 93 calculates blood vessel information for each pixel of the endoscope image. For example, blood vessel information of one pixel is calculated using the data of pixels in a predetermined range including a pixel whose blood vessel information is to be calculated (for example, a range of 99×99 pixels centered on the pixel whose blood vessel information is to be calculated). For example, in the case of calculating the thickness of a blood vessel as blood vessel information, the "thickness of a blood vessel" for each pixel is a statistic of the thickness of a blood vessel in the predetermined range. The statistic is a so-called basic statistic, and is, for example, a maximum value, a minimum, an average value, a median, or a mode. Needless to say, it is also possible to use statistics other than the exemplified values. For example, a value (ratio between the maximum value and the minimum value or the like) calculated using a so-called representative value, such as the maximum value, the minimum value, the average value, the median, or the mode, or a so-called scattering degree, such as a dispersion, a standard deviation, and a variation coefficient, can be used.

In the case of setting a region of interest, the blood vessel information calculation unit 93 calculates a statistic of blood vessel information of each pixel included in the region of interest, and sets the value as blood vessel information of the region of interest. For example, in the case of calculating the thickness of a blood vessel as blood vessel information, the "thickness of a blood vessel" of each pixel is calculated as described above. In a case where a region of interest is set, a statistic of the "thickness of a blood vessel" of each pixel included in the region of interest is further calculated, and one "thickness of a blood vessel" is calculated for one set region of interest. The same is true for a case where the entire endoscope image is set as a region of interest.

The statistic in the case of calculating blood vessel information for each pixel and the statistic in the case of calculating blood vessel information of a region of interest may be the same statistic, or may be different. For example, in the case of calculating the thickness of a blood vessel for each pixel, an average value of the thickness of the blood vessel appearing in a "predetermined range" may be calculated. Thereafter, even in the case of calculating the thickness of a blood vessel in the region of interest, the average value of the thickness of the blood vessel of each pixel may be calculated, or a mode of the thickness of the blood vessel of each pixel may be calculated.

In the present embodiment, blood vessel information is calculated for each pixel as described above and then the statistic of the blood vessel information calculated for each pixel within the region of interest is calculated, thereby calculating the blood vessel information of the region of interest. However, depending on the type of blood vessel information to be calculated, a relationship between the method of calculating the statistic in the case of calculating the blood vessel information for each pixel and the method of calculating the statistic in the case of calculating the blood vessel information of the region of interest, and the like, it is possible to omit the blood vessel information for each pixel. In the case of the "thickness of a blood vessel", an average value of the thickness of the blood vessel appearing in the region of interest can be set as the thickness of the blood vessel in the region of interest.

The blood vessel parameter calculation unit 94 calculates an evaluation value, which is called a blood vessel parameter relevant to a blood vessel at a specific depth, by calculation using the blood vessel information calculated by the blood vessel information calculation unit 93. In the present embodiment, the blood vessel parameter calculation unit 94 calculates a blood vessel parameter using a plurality of pieces of blood vessel information. Specifically, in a case where the surface layer blood vessel 74 is extracted by the blood vessel extraction unit 92, the blood vessel parameter calculation unit 94 calculates a blood vessel parameter relevant to the surface layer blood vessel 74 by calculation using a plurality of pieces of blood vessel information regarding the surface layer blood vessel 74. Similarly, in a case where the middle deep layer blood vessel 75 is extracted by the blood vessel extraction unit 92, the blood vessel parameter calculation unit 94 calculates a blood vessel parameter relevant to the middle deep layer blood vessel 75 by calculation using a plurality of pieces of blood vessel information regarding the middle deep layer blood vessel 75.

The blood vessel parameter calculation unit 94 calculates a blood vessel parameter by multiplying each of the plurality of pieces of blood vessel information by a weighting coefficient and taking a sum thereof. The weighting coefficient is stored in a weighting coefficient table 99, and is determined in advance, for example, by machine learning. In the present embodiment, in the case of calculating a blood vessel parameter relevant to the surface layer blood vessel 74 and the case of calculating a blood vessel parameter relevant to the middle deep layer blood vessel 75, the weighting coefficient table 99 is commonly used. Therefore, in the case of calculating the blood vessel parameter relevant to the surface layer blood vessel 74 and the case of calculating the blood vessel parameter relevant to the middle deep layer blood vessel 75, the content of the calculation is common.

In the present embodiment, the blood vessel parameter calculation unit 94 calculates the weighted sum of a plurality of pieces of blood vessel information as a blood vessel parameter as described above. However, the method of calculating the blood vessel parameter is arbitrary. For example, a blood vessel parameter may be calculated by operation including addition, subtraction, multiplication, and division instead of simply taking a sum, or a blood vessel parameter may be calculated using other functions. In a case where it is necessary to change the method of calculating a blood vessel parameter according to the depth of the blood vessel, a weighting coefficient table is provided for each depth of the blood vessel. For example, in a case where a first weighting coefficient table used in the case of calculating a blood vessel parameter relevant to the surface layer blood vessel 74 and a second weighting coefficient table used in the case of calculating a blood vessel parameter relevant to the middle deep layer blood vessel 75 are prepared in advance as the weighting coefficient table 99, the method of calculating a blood vessel parameter can be changed between the surface layer and the middle deep layer.

In a case where it is necessary to change the method of calculating a blood vessel parameter according to the depth of the blood vessel, the blood vessel parameter calculation unit 94 stores a weighting coefficient for each depth of the blood vessel in advance. The blood vessel parameter calculation unit 94 can calculate a plurality of types of blood vessel parameters. For example, the blood vessel parameter calculation unit 94 can calculate a blood vessel parameter PA relevant to a lesion A and a blood vessel parameter PB relevant to a lesion B different from the lesion A. The blood vessel parameter PA and the blood vessel parameter PB have different weighting coefficients used at the time of calculation. Therefore, the blood vessel parameter calculation unit 94 stores a plurality of weighting coefficients in advance for each blood vessel parameter. As described above, the weighting coefficient table 99 stores weighting coefficients for each depth or for each type of blood vessel parameter.

Since the blood vessel parameters are calculated by adding pieces of blood vessel information having different dimensions (units) or the like, the blood vessel parameters have no physical meaning but function as indices of diagnosis. That is, unlike the blood vessel information, the blood vessel parameter is a value having no physical meaning.

Figure 8:
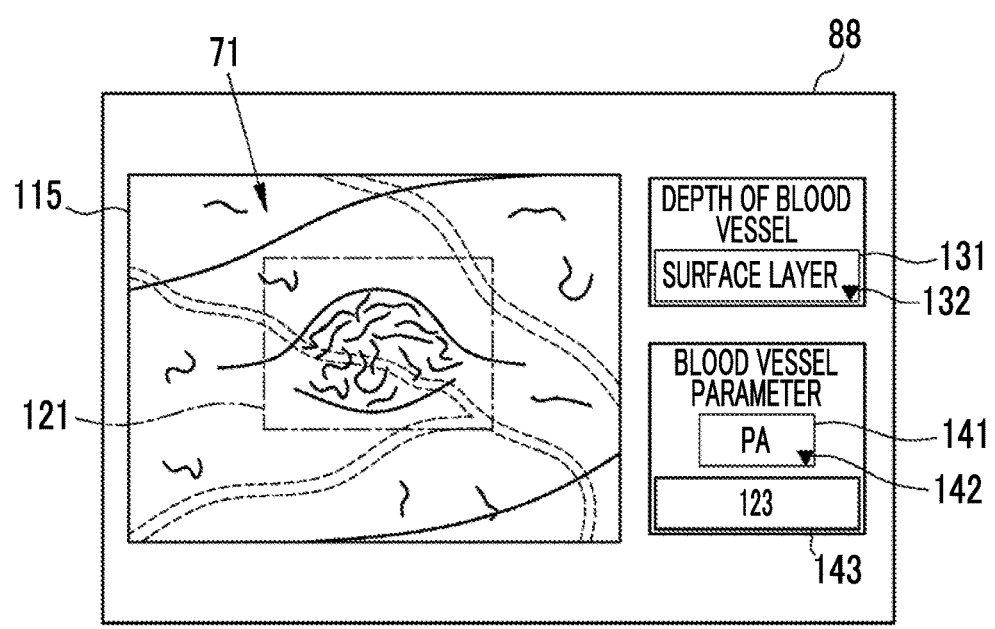
FIG. 8 is a display screen of a monitor.

The display control unit 95 controls the display of the monitor 98. For example, as shown in FIG. 8, the display control unit 95 displays the endoscope image acquired by the image acquisition unit 91 on the monitor 98. In the case of the present embodiment, since the image acquisition unit 91 acquires two types of endoscope images of the first endoscope image 71 and the second endoscope image 72, the display control unit 95 displays the first endoscope image 71 of these images in an endoscope image display portion 115. By changing the display setting, the second endoscope image 72 of the first endoscope image 71 and the second endoscope image 72 can be displayed in the endoscope image display portion 115. The display control unit 95 can also display a composite image, which is obtained by combining the first endoscope image 71 and the second endoscope image 72, in the endoscope image display portion 115. For example, the composite image is an image having high visibility of the surface layer blood vessel 74 to the same extent as the first endoscope image 71 and high visibility of the middle deep layer blood vessel 75 to the same extent as the second endoscope image 72. In this case, the display control unit 95 also functions as an image combining unit. A region of interest 121 is designated in an endoscope image (in the present embodiment, the first endoscope image 71) displayed in the endoscope image display portion 115. The input device 97 is used to designate the region of interest 121.

By acquiring information regarding the type of the acquired endoscope image from the image acquisition unit 91, the display control unit 95 generates a list of depths extractable by the blood vessel extraction unit 92 using the endoscope image acquired by the image acquisition unit 91, and displays the list in a depth setting portion 131. In the depth setting portion 131, the above list is displayed by operating a pull-down button 132, for example. In the case of the present embodiment, since the image acquisition unit 91 acquires the first endoscope image 71 and the second endoscope image 72, the extractable blood vessel depth is "surface layer" or "middle deep layer". Therefore, in a case where the pull-down button 132 is operated, the "surface layer" and the "middle deep layer" are displayed as a list in the depth setting portion 131. In the depth setting portion 131 shown in FIG. 8, a state in which the "surface layer" is selected from the "surface layer" and the "middle deep layer" is shown. Instead of displaying a list of extractable depths in the depth setting portion 131, the depth of a blood vessel to be extracted may be able to be input as a numerical value. In this case, a "specific depth" including the numerical value input to the depth setting portion 131 is set to the depth of a blood vessel to be extracted. For example, in a case where "40 (μm)" is input to the depth setting portion 131, the setting is made to extract the surface layer blood vessel 74 from the surface layer blood vessel 74 and the middle deep layer blood vessel 75.

The blood vessel extraction unit 92 determines the depth of the blood vessel to be extracted according to the setting of the depth setting portion 131. In a case where the "surface layer" is selected in the depth setting portion 131, the blood vessel extraction unit 92 extracts the surface layer blood vessel 74. In a case where the "middle deep layer" is selected in the depth setting portion 131, the blood vessel extraction unit 92 extracts the middle deep layer blood vessel 75.

The display control unit 95 acquires the types of blood vessel parameters that can be calculated from the blood vessel parameter calculation unit 94 (or stores in advance), and displays these in a blood vessel parameter setting portion 141. In the blood vessel parameter setting portion 141, a list of the above blood vessel parameters is displayed by operating a pull-down button 142, for example. More specifically, in a case where the blood vessel parameter PA relevant to the lesion A and the blood vessel parameter PB relevant to the lesion B can be calculated, "PA" or "PB" is displayed as a list by operating the pull-down button 142. In the blood vessel parameter setting portion 141 shown in FIG. 8, a state of the setting for calculating the blood vessel parameter PA is shown.

According to the setting of the blood vessel parameter setting portion 141, the blood vessel parameter calculation unit 94 selects a weighting coefficient corresponding to the setting from the weighting coefficient table 99 and uses the weighting coefficient. For example, in the case of setting for calculating the blood vessel parameter PA as in FIG. 8, the blood vessel parameter calculation unit 94 calculates the blood vessel parameter PA by selecting a weighting coefficient, which is used for calculating the blood vessel parameter PA, from the weighting coefficient table 99 and using the weighting coefficient. The display control unit 95 displays the value of the blood vessel parameter calculated by the blood vessel parameter calculation unit 94 in a blood vessel parameter display portion 143. In the case shown in FIG. 8, the value of the blood vessel parameter PA is "123".

Figure 9:
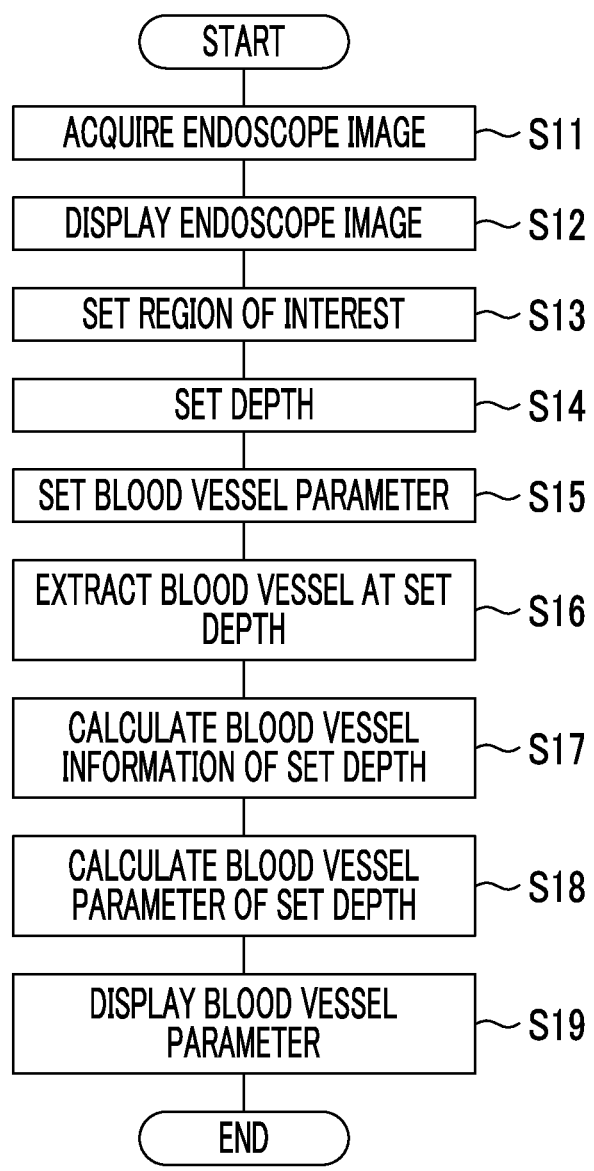
FIG. 9 is a flowchart showing the operation of the image processing apparatus.

Next, the flow of the operation of the image processing apparatus 65 will be described with reference to a flowchart shown in FIG. 9. First, according to the input operation of the input device 97, the image processing apparatus 65 acquires the first endoscope image 71 and the second endoscope image 72 from the storage 64 using the image acquisition unit 91 (S11), and displays these images on the monitor 98 (S12). Of the first endoscope image 71 and the second endoscope image 72 that have been acquired, the image processing apparatus 65 displays the first endoscope image 71, or the second endoscope image 72, or a composite image of the first endoscope image 71 and the second endoscope image 72 in the endoscope image display portion 115 according to the setting. In the present embodiment, the first endoscope image 71 is displayed in the endoscope image display portion 115.

In a case where the first endoscope image 71 is displayed on the monitor 98, the doctor sets the region of interest 121 by operating the input device 97 (S13). For example, in a case where there is an attention portion, which requires diagnosis of whether or not there is a lesion (or the degree of progress of a lesion or the like), in the vicinity of the approximate center of the first endoscope image 71, a region including the attention portion is set as the region of interest 121 (refer to FIG. 8).

Then, the doctor sets the depth of the blood vessel in the depth setting portion 131 by operating the input device 97 (S14), and sets the type of the blood vessel parameter to be calculated in the blood vessel parameter setting portion 141 (S15). In the present embodiment, the "surface layer" is set in the depth setting portion 131, and "PA" (blood vessel parameter PA relevant to the lesion A) is set in the blood vessel parameter setting portion 141. Therefore, the blood vessel extraction unit 92 extracts the surface layer blood vessel 74 using the first endoscope image 71 and the second endoscope image 72 (S16), the blood vessel information calculation unit 93 calculates a plurality of pieces of blood vessel information regarding the extracted surface layer blood vessel 74 (S17), and the blood vessel parameter calculation unit 94 calculates the blood vessel parameter PA by calculation using the plurality of pieces of blood vessel information calculated by the blood vessel information calculation unit 93 (S18). The value of the blood vessel parameter PA calculated by the blood vessel parameter calculation unit 94 is displayed in the blood vessel parameter display portion 143 (S19).

As described above, the image processing apparatus 65 calculates more intuitive and useful blood vessel parameters than blood vessel information not only by calculating various kinds of blood vessel information but also by performing calculation using a plurality of pieces of blood vessel information. The blood vessel parameter calculated by the image processing apparatus 65 is a blood vessel parameter relevant to a blood vessel at a specific depth of the observation target. Accordingly, the image processing apparatus 65 can assist diagnosis more directly than conventional endoscope systems and the like that simply calculate blood vessel information. In addition, it is possible to assist diagnosis more effectively than conventional endoscope systems and the like that calculate blood vessel information for each submucosal depth.

In the first embodiment described above, the depth of a blood vessel to be extracted is set, and a blood vessel parameter is calculated for a blood vessel at the set depth. However, the blood vessel extraction unit 92 may extract a blood vessel for each depth, the blood vessel information calculation unit 93 may calculate a plurality of pieces of blood vessel information for each depth of the observation target, and the blood vessel information calculation unit 93 may calculate the blood vessel parameter of each depth by using the plurality of pieces of blood vessel information calculated for each depth.

Figure 10:
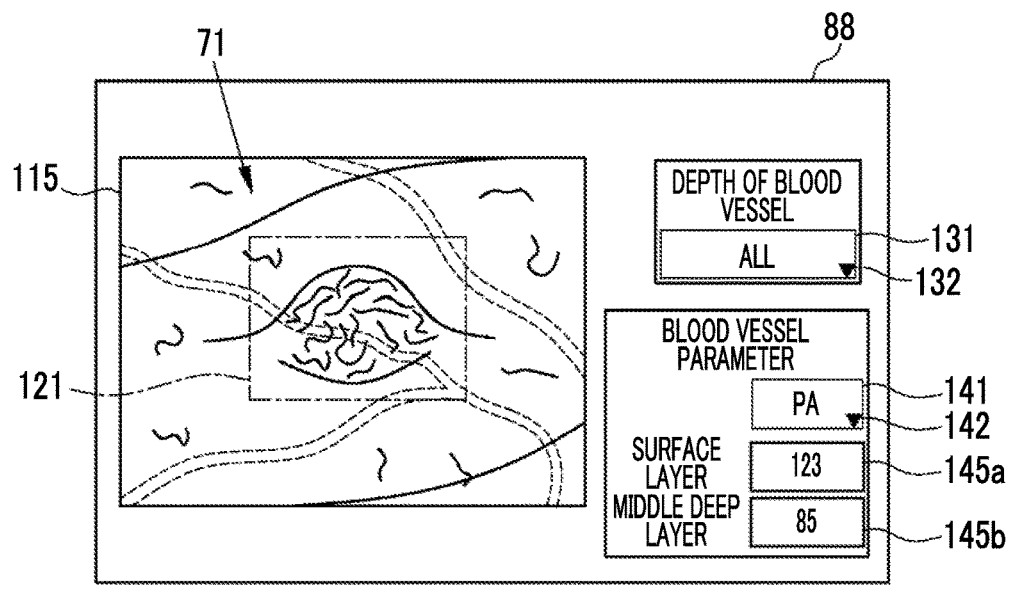
FIG. 10 is a display screen of a monitor in the case of calculating a blood vessel parameter for each depth.

For example, as shown in FIG. 10, a setting "ALL" for extracting all blood vessels for each depth is prepared in the depth setting portion 131. In a case where the first endoscope image 71 and the second endoscope image 72 are used, "ALL" is a setting in which the blood vessel extraction unit 92 extracts the surface layer blood vessel 74 and extracts the middle deep layer blood vessel 75 using the first endoscope image 71 and the second endoscope image 72. Therefore, the blood vessel information calculation unit 93 calculates a plurality of pieces of blood vessel information regarding the surface layer blood vessel 74, and calculates a plurality of pieces of blood vessel information regarding the middle deep layer blood vessel 75. Then, according to the setting (in FIG. 10, the setting for calculating the blood vessel parameter "PA") of the blood vessel parameter setting portion 141, the blood vessel parameter calculation unit 94 calculates a blood vessel parameter of the "surface layer" by calculation using a plurality of pieces of blood vessel information regarding the surface layer blood vessel 74, and calculates a blood vessel parameter of the "middle deep layer" by calculation using a plurality of pieces of blood vessel information regarding the middle deep layer blood vessel 75. Then, the display control unit 95 provides a first blood vessel parameter display portion 145a for displaying the blood vessel parameter of the surface layer and a second blood vessel parameter display portion 145b for displaying the blood vessel parameter of the middle deep layer, instead of the blood vessel parameter display portion 143, and displays the value of each calculated blood vessel parameter in these blood vessel parameter display portions. In FIG. 10, a value "123" of the blood vessel parameter PA relevant to the surface layer blood vessel 74 is displayed in the first blood vessel parameter display portion 145a, and a value "85" of the blood vessel parameter PA relevant to the middle deep layer blood vessel 75 is displayed in the second blood vessel parameter display portion 145b.

As described above, in a case where a blood vessel is extracted for each of a plurality of depths and a blood vessel parameter of each depth is calculated, it is possible to compare blood vessel parameters for each depth. As a result, it is possible to assist diagnosis more satisfactorily. The same is true for a case where the depth with the mucosal surface as a reference is divided into three or more layers, such as "surface layer", "middle layer", and "deep layer", and a blood vessel parameter is calculated for each depth.

Figure 11:
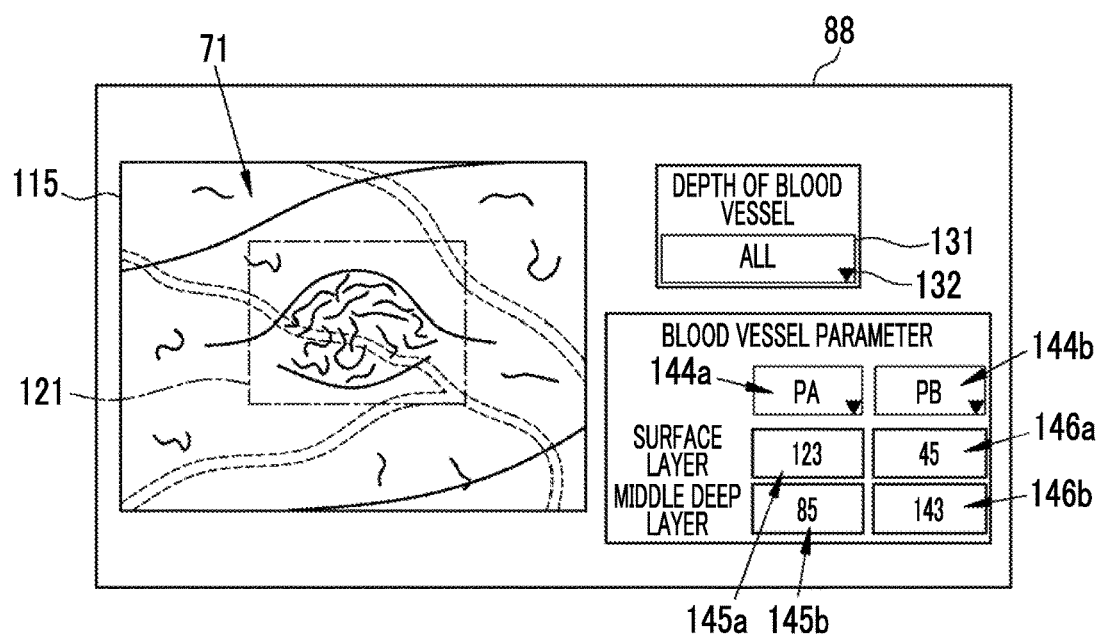
FIG. 11 is a display screen of a monitor in the case of calculating a plurality of types of blood vessel parameters.

In the modification example described above, the setting for calculating the blood vessel parameter PA is performed by the blood vessel parameter setting portion 141, and the blood vessel parameter PA is calculated for each depth. However, in a case where the blood vessel parameter calculation unit 94 can calculate a plurality of types of blood vessel parameters, two or more types of blood vessel parameters may be calculated. For example, in a case where the blood vessel parameter PA relevant to the lesion A and the blood vessel parameter PB relevant to the lesion B can be calculated as blood vessel parameters, a first blood vessel parameter setting portion 144a and a second blood vessel parameter setting portion 144b are provided instead of the blood vessel parameter setting portion 141 as shown in FIG. 11. Then, for each depth, the blood vessel parameter PA and the blood vessel parameter PB are calculated and displayed. Specifically, a value "123" of the blood vessel parameter PA of the "surface layer" is displayed in the first blood vessel parameter display portion 145a, and a value "85" of the blood vessel parameter PA of the "middle deep layer" is displayed in the second blood vessel parameter display portion 145b. Similarly, a value "45" of the blood vessel parameter PB of the "surface layer" is displayed in a blood vessel parameter display portion 146a, and a value "143" of the blood vessel parameter PB of the "middle deep layer" is displayed in the blood vessel parameter display portion 146b.

By calculating a plurality of types of blood vessel parameters as described above, it is possible to perform diagnosis from different viewpoints at the same time. As a result, it is possible to assist diagnosis more satisfactorily. The same is true for a case of calculating three or more blood vessel parameters.

Figure 12:
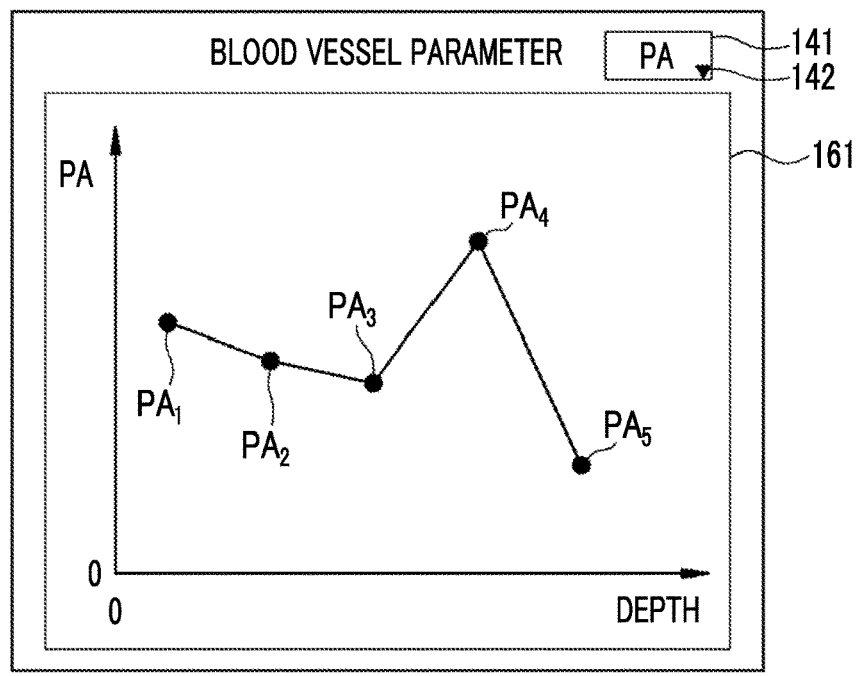
FIG. 12 is a graph showing a change of a blood vessel parameter with respect to a depth.

In the first embodiment described above, the calculated blood vessel parameters are displayed numerically in the blood vessel parameter display portion 143. However, in a case where the blood vessel parameter calculation unit 94 calculates a plurality of blood vessel parameters for each depth, the calculated blood vessel parameters for each depth may be displayed as a graph with respect to the depth. For example, in the case of calculating the blood vessel parameter PA for each of a first specific depth, a second specific depth, a third specific depth, a fourth specific depth, and a fifth specific depth, a blood vessel parameter $PA_1$ of the first specific depth, a blood vessel parameter $PA_2$ of the second specific depth, a blood vessel parameter $PA_3$ of the third specific depth, a blood vessel parameter $PA_4$ of the fourth specific depth, and a blood vessel parameter $PA_5$ of the fifth specific depth can be displayed on the monitor 98 as a graph 161 with respect to the depth, as shown in FIG. 12. In a case where the blood vessel parameter calculated for each depth is displayed as the graph 161 with respect to the depth as described above, changes or abnormalities of the blood vessel parameter due to the depth can be easily found visually. As a result, it is possible to assist diagnosis more satisfactorily.

In the first embodiment and the modification example described above, a blood vessel parameter of a specific depth is calculated using a plurality of pieces of blood vessel information calculated for a blood vessel at the specific depth. For example, a blood vessel parameter of the "surface layer" is calculated using a plurality of pieces of blood vessel information calculated for the blood vessel of the "surface layer", and a blood vessel parameter of the "middle deep layer" is calculated using a plurality of pieces of blood vessel information calculated for the blood vessel of the "middle deep layer". However, the blood vessel parameter calculation unit 94 may calculate the blood vessel information of a specific depth using blood vessel information calculated for blood vessels having depths other than the specific depth. For example, in the case of calculating the blood vessel parameter of the "surface layer", it is possible to use not only the blood vessel information regarding the blood vessel of the "surface layer" but also the blood vessel information regarding the blood vessel of the "middle deep layer". Similarly, in the case of calculating the blood vessel parameter of the "middle deep layer", it is possible to use not only the blood vessel information regarding the blood vessel of the "middle deep layer" but also the blood vessel information regarding the blood vessel of the "surface layer". Depending on the type of the blood vessel parameter, in a case where pieces of blood vessel information between different depths are used in combination as described above, a more accurate and useful value may be obtained.

Figure 13:
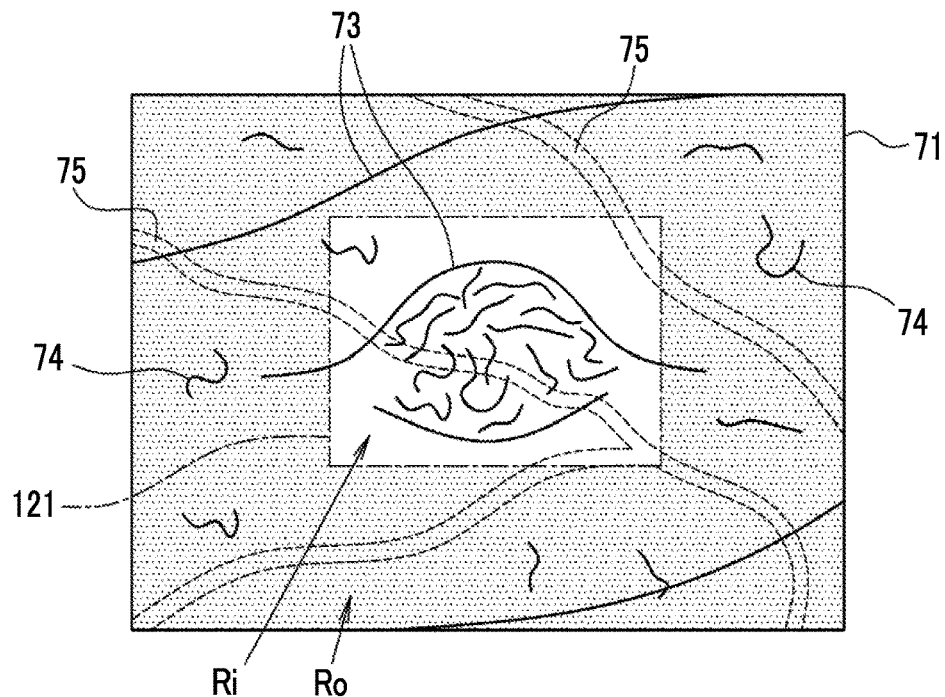
FIG. 13 is an explanatory diagram showing the inside and outside of a region of interest.

In the first embodiment and the modification example described above, blood vessel information is calculated for the set region of interest 121, and the blood vessel parameter of the region of interest 121 is calculated by calculation using the blood vessel information of the region of interest 121. However, even in the case of designating the region of interest 121, blood vessel information of a region other than the region of interest 121 can be used. For example, as shown in FIG. 13, the blood vessel information calculation unit 93 calculates blood vessel information for the inside Ri of the region of interest 121 in the same manner as in the first embodiment or the like, and also calculates blood vessel information for a region Ro other than the region of interest 121. Then, the blood vessel parameter calculation unit 94 calculates the blood vessel parameter using not only the blood vessel information calculated for the inside Ri of the region of interest 121 but also the blood vessel information calculated for the region Ro other than the region of interest 121. In this manner, in a case where the blood vessel information calculated for the region Ro other than the region of interest 121 is also used in the calculation of the blood vessel parameter, it is possible to calculate a more accurate blood vessel parameter since the individual difference of the observation target is reduced from the blood vessel parameter. The region Ro other than the region of interest 121 is a normal part of the observation target in general. Therefore, the influence of the individual difference of the observation target on the blood vessel parameter is reduced, for example, by standardizing the blood vessel information according to "normal" blood vessel information unique to the observation target.

Second Embodiment

Figure 14:
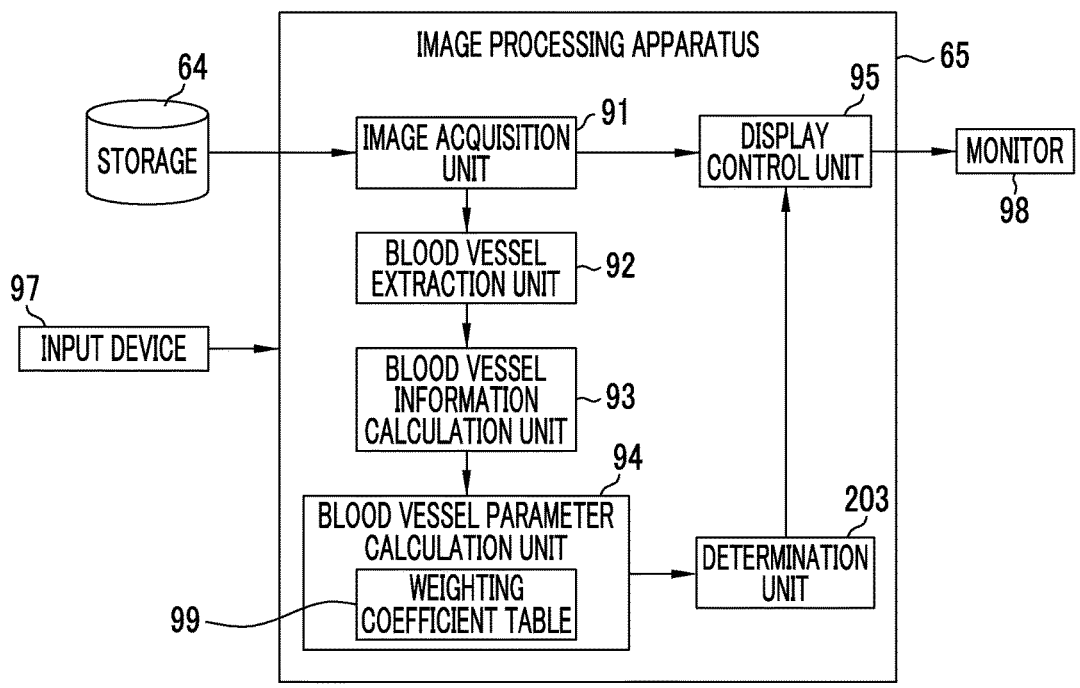
FIG. 14 is a block diagram of an image processing apparatus of a second embodiment.

In the first embodiment and the modification example described above, a blood vessel parameter is calculated and displayed on the monitor 98. However, as shown in FIG. 14, a determination unit 203 for determining the state of the mucous membrane of the observation target using a blood vessel parameter may be provided in the image processing apparatus 65, and the determination result of the determination unit 203 may be displayed on the monitor 98. The "state of the mucous membrane" of the observation target is a comprehensive status as the entire mucous membrane including blood vessels. For example, the "state of the mucous membrane" of the observation target is "normal", "adenoma" (suspected of adenoma), "cancer" (suspected of cancer), and the like.

The determination unit 203 acquires a blood vessel parameter from the blood vessel parameter calculation unit 94, and determines the state of the mucous membrane of the observation target based on the blood vessel parameter or by performing further calculation using the blood vessel parameter.

Figure 15:
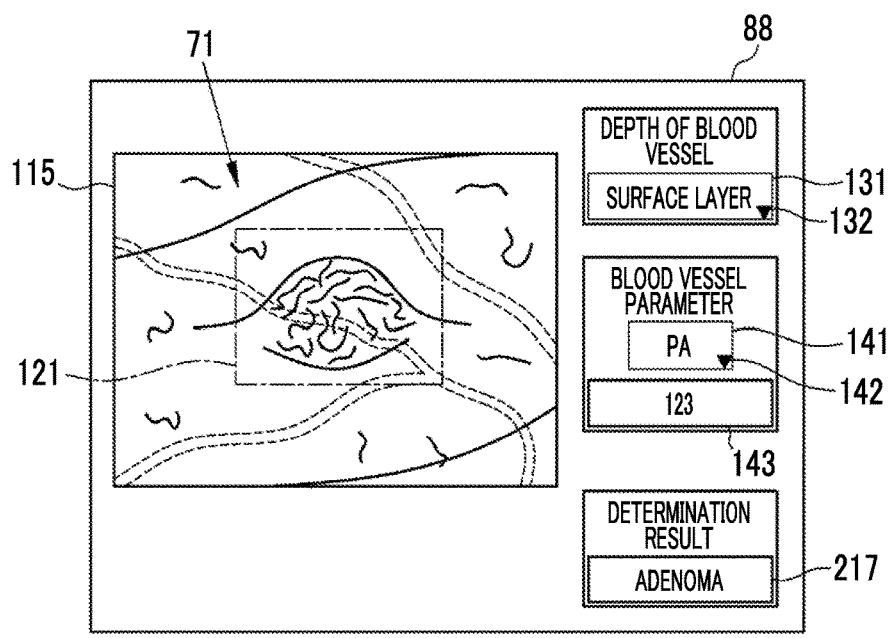
FIG. 15 is a display screen of a monitor for displaying the determination result of a determination unit.

For example, it is assumed that a weighting coefficient used for calculating the blood vessel parameter PA is set as a balance for determining the state of the mucous membrane to be one of three kinds of states (normal, adenoma, and cancer). In this case, the determination unit 203 determines the state of the mucous membrane of the observation target to be "normal" in a case where the blood vessel parameter PA is equal to or less than a first threshold value TH1. In a case where the blood vessel parameter PA is greater than the first threshold value TH1 and equal to or less than a second threshold value TH2, the determination unit 203 determines the state of the mucosa of the observation target to be "adenoma". In a case where the blood vessel parameter PA is greater than the second threshold value TH2, the determination unit 203 determines the state of the mucosa of the observation target to be "cancer". Then, as shown in FIG. 15, a determination result display portion 217 is provided on the display screen of the monitor 98 to display the determination result of the determination unit 203 described above. In the case shown in FIG. 15, the determination result is "adenoma".

As described above, by providing the determination unit 203 in the image processing apparatus 65, determining the state of the mucous membrane of the observation target using the blood vessel parameter, and displaying the determination result 208, it is possible to assist the diagnosis so as to be easily understood in a more straightforward way than in a case where the blood vessel parameter is displayed.

It is desirable that the determination unit 203 determines the state of the mucous membrane to be three or more states including normal, adenoma, and cancer. In particular, in the case of determining the state of the mucous membrane of the large intestine, it is preferable to determine the state of the mucous membrane of the large intestine to be any state including normal, hyperplastic polyp (HP), sessile serrated adenoma/Polyp (SSA/P), traditional serrated adenoma (TSA), laterally spreading tumor (LST), and cancer. In a case where the determination result of the determination unit 203 is subdivided as described above, it is preferable that the determination unit 203 uses blood vessel information in addition to the blood vessel parameter. Conventionally, a hyperplastic polyp was thought to have low risk of canceration and does not need to be treated. In recent years, however, an example in which an SSA/P analogous to a hyperplastic polyp is cancerated has also been discovered. In particular, it is becoming important to differentiate between the hyperplastic polyp and the SSA/P. On the other hand, it is known that an SSA/P is likely to be formed in a case where the middle deep layer blood vessel 75 traverses under the thickened mucous membrane thought to be a hyperplastic polyp or SSA/P. By using the blood vessel parameter, the determination unit 203 can differentiate between the hyperplastic polyp and the SSA/P. However, by using the blood vessel parameter and the blood vessel information (thickness and length of a blood vessel) in combination, it is possible to differentiate between the hyperplastic polyp and the SSA/P with a higher probability.

In a case where the state of the mucous membrane of the observation target is cancer, it is preferable that the determination unit 203 further determines the stage of cancer using the blood vessel parameter. Then, it is preferable to display the stage of the cancer determined by the determination unit 203 in the determination result display portion 217. In this manner, in a case where the state of the mucous membrane of the observation target is determined to be cancer, the stage is further determined and the result is displayed on the monitor 98, so that the diagnosis can be more finely assisted. In a case where the state of the mucous membrane of the observation target is cancer and the stage of the cancer is further determined, the stage of the cancer may be determined by combining the blood vessel parameter with the blood vessel information or by using the blood vessel information.

In the second embodiment described above, the determination result of the determination unit 203 is displayed on the monitor 98. However, instead of displaying the determination result itself of the determination unit 203 on the monitor 98, a warning may be displayed based on the determination result of the determination unit 203. For example, in a case where the determination result of the determination unit 203 is "cancer", it is preferable to display a warning message based on the determination result, such as "there is a possibility of cancer", in the determination result display portion 217.

In the second embodiment described above, the determination unit 203 determines the state of the mucous membrane of the observation target by comparing the blood vessel parameter with the first threshold value TH1 and the second threshold value TH2. However, as in the modification example of the first embodiment, in the case of calculating the blood vessel parameter for each of a plurality of depths, the state of the mucous membrane of the observation target can be determined according to the change of the blood vessel parameter with respect to the depth.

For example, it is assumed that the blood vessel parameter PA is calculated for each of the first specific depth, the second specific depth, the third specific depth, the fourth specific depth, and the fifth specific depth and the blood vessel parameter PA has a property of decreasing as the depth with respect to the mucosal surface increases in a case where the observation target is normal. Then, in a case where any of the blood vessel parameter $PA_1$ of the first specific depth, the blood vessel parameter $PA_2$ of the second specific depth, the blood vessel parameter $PA_3$ of the third specific depth, the blood vessel parameter $PA_4$ of the fourth specific depth, and the blood vessel parameter $PA_5$ of the fifth specific depth that have been calculated is different from the change mode expected in the case of the observation target, the determination unit 203 can determine the state of the mucous membrane of the observation target to be abnormal (adenoma, cancer, or the like). For example, as shown in FIG. 16, based on the fact that the blood vessel parameter $PA_4$ of the fourth specific depth deviates from a change width 218 expected in a case where the state of the mucous membrane of the observation target is normal, the determination unit 203 determines the state of the mucous membrane of the observation target to be abnormal.

In the case of determining the state of the mucous membrane of the observation target based on the change mode of the blood vessel parameter with respect to the depth, the "change mode of the blood vessel parameter with respect to the depth" expected in a case where the observation target is normal differs depending on the blood vessel parameter. In addition to the blood vessel parameter that decreases as the depth increases as described above, there is also a blood vessel parameter that increases as the depth increases conversely. There is also a blood vessel parameter by which it can be determined that there is a possibility of lesion in a case where the value is small at the surface layer, increases at the middle layer, and decreases again at the deep layer. In the case of a blood vessel parameter that is almost fixed regardless of depth, the state of the mucous membrane of the observation target can be determined to be abnormal in a case where the value of the blood vessel parameter deviates from the fixed value at any of the depths at which the blood vessel parameter is calculated, such as the surface layer, the middle layer, or the deep layer.

Figure 16:
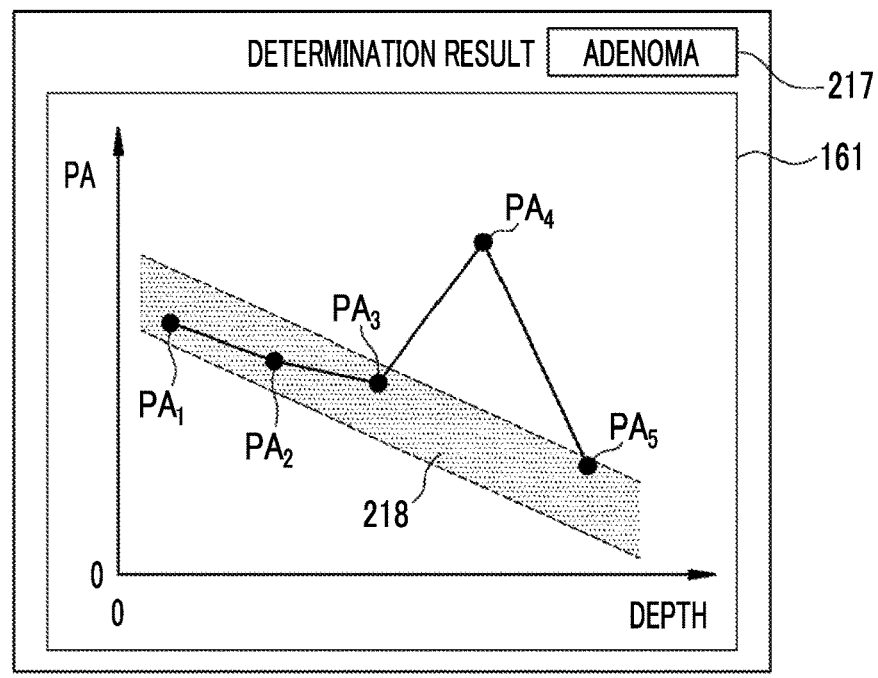
FIG. 16 is a part of the display screen of the monitor in the case of determining the state of the mucous membrane according to the change of the blood vessel parameter with respect to the depth.

As described above, in the case of determining the state of the mucous membrane of the observation target based on the change mode of the blood vessel parameter with respect to the depth, it is preferable that the change of the blood vessel parameter with respect to the depth is displayed on the monitor 98 as shown in FIG. 16 to indicate the basis of the determination of the determination unit 203.

Figure 17:
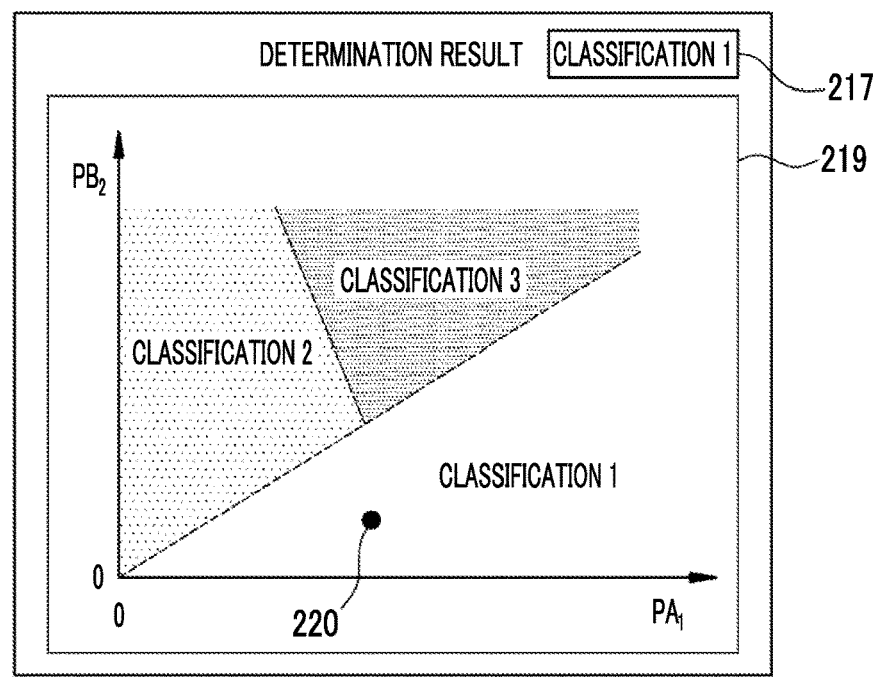
FIG. 17 is a part of the display screen of the monitor in the case of determining the state of the mucous membrane based on a plurality of blood vessel parameters.

In the second embodiment described above, the determination unit 203 determines the state of the mucous membrane of the observation target using one type of blood vessel parameter, the state of the mucous membrane of the observation target may also be determined using a plurality of types of blood vessel parameters. For example, as shown in FIG. 17, the state of the mucous membrane of the observation target may be able to be divided into classification 1, classification 2, and classification 3 (normal, adenoma, cancer, and the like) according to the relationship between the blood vessel parameter $PA_1$ of the first depth and the blood vessel parameter $PB_2$ of the second depth. In this case, as shown in FIG. 17, it is preferable that a graph 219 showing a classification based on the relationship between a plurality of blood vessel parameters used in the determination of the determination unit 203 and values 220 of the plurality of calculated blood vessel parameters are displayed on the monitor 98 to indicate the basis of the determination of the determination unit 203.

Third Embodiment

Figure 18:
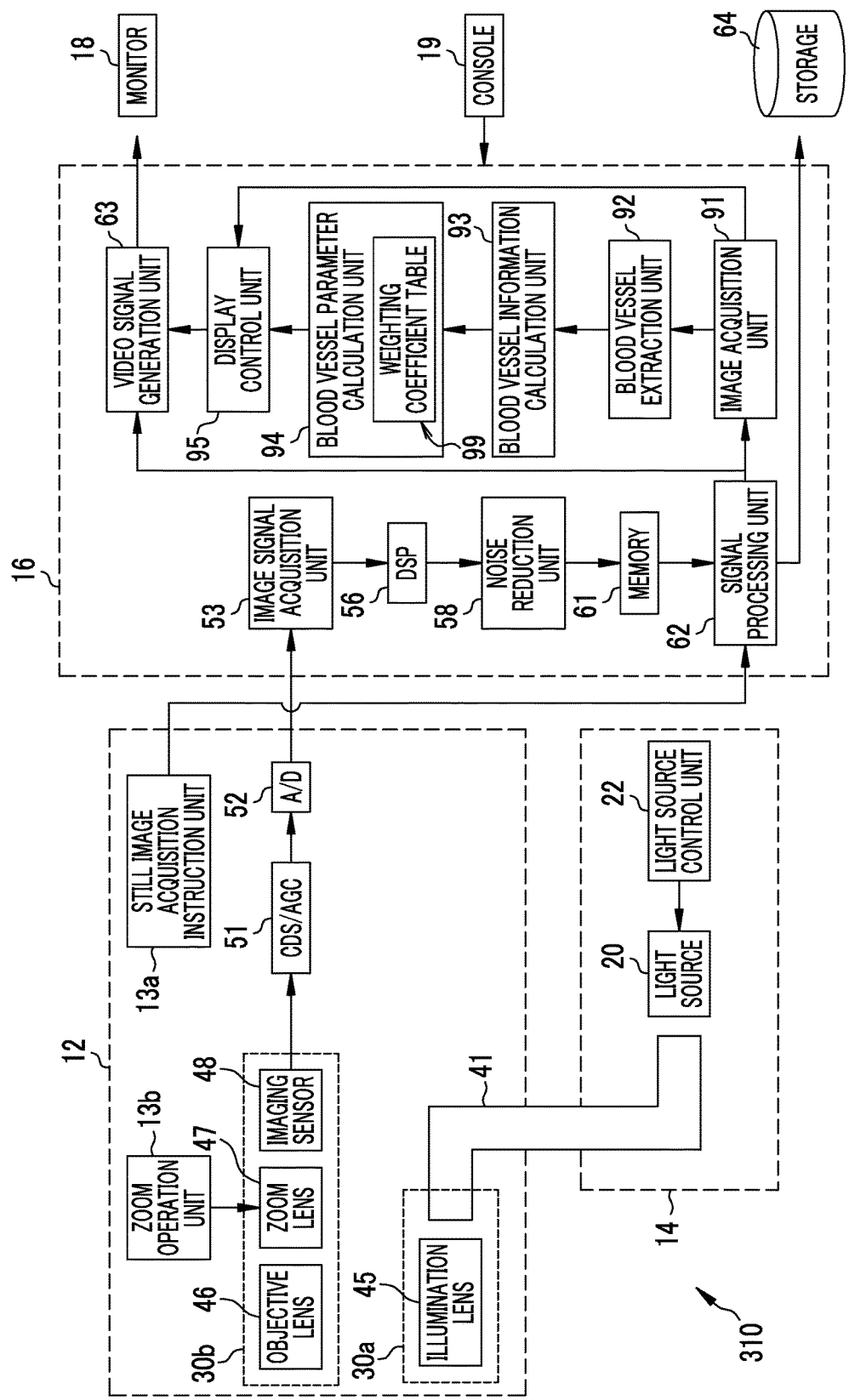
FIG. 18 is a block diagram of an endoscope system of a third embodiment.

In the first and second embodiments described above, the endoscope system 10 stores an endoscope image in the storage 64, and the image processing apparatus 65 acquires the endoscope image from the storage 64 later to calculate a blood vessel parameter. However, the endoscope system 10 may calculate a blood vessel parameter almost in real time while observing the observation target. In this case, as in an endoscope system 310 shown in FIG. 18, the image acquisition unit 91, the blood vessel extraction unit 92, the blood vessel information calculation unit 93, the blood vessel parameter calculation unit 94, and the display control unit 95 are provided in the processor device 16. The configuration of the endoscope 12 or the light source device 14 is the same as that of the endoscope system 10 of the first embodiment.

In a case where each unit of the image processing apparatus 65 is provided in the processor device 16 as described above, the image acquisition unit 91 can directly acquire the endoscope image generated by the signal processing unit 62 from the signal processing unit 62 without passing through the storage 64. Therefore, the image acquisition unit 91 acquires the first endoscope image 71 and the second endoscope image 72 generated in a case where a still image acquisition instruction is input, for example. The operations of the blood vessel extraction unit 92, the blood vessel information calculation unit 93, the blood vessel parameter calculation unit 94, and the display control unit 95 other than the image acquisition unit 91 are the same as those in the endoscope system 10 of the first embodiment.

As described above, in a case where each unit of the image processing apparatus 65 is provided in the processor device 16, the processor device 16 also functions as the image processing apparatus 65. Therefore, in the endoscope system 310, since a blood vessel parameter can be calculated while observing the observation target, it is possible to assist the diagnosis almost in real time. The endoscope system 310 is suitable for a case of administering a medicine to the observation target or performing an operation on the observation target and observing the action.

In the third embodiment described above, the image acquisition unit 91 directly acquires the endoscope image generated by the signal processing unit 62. However, instead of directly acquiring the endoscope image from the signal processing unit 62, the first endoscope image 71 and the second endoscope image 72 may be acquired from the storage 64 as in the first embodiment or the like.

In the third embodiment described above, the endoscope image acquired by the image acquisition unit 91 from the signal processing unit 62 is an endoscope image generated in a case where a still image acquisition instruction is input. However, the blood vessel parameter may be calculated using the first endoscope image 71 and the second endoscope image 72 sequentially generated in the special observation mode regardless of the still image acquisition instruction. In this case, it is preferable that the setting of a region of interest, extraction of a blood vessel, calculation of blood vessel information, and calculation of a blood vessel parameter are automatically performed at predetermined time intervals. The time interval for calculating the blood vessel parameter can be arbitrarily set by the doctor.

In the first to third embodiments described above, two endoscope images of the first endoscope image 71 and the second endoscope image 72 are used for calculation of blood vessel parameters. However, blood vessel parameters may be calculated using three or more endoscope images. In a case where three or more endoscope images are used, it is possible to extract blood vessels and finely set (select) the "specific depth" to calculate blood vessel parameters.

In the first to third embodiments described above, blood vessel parameter calculation unit 94 calculates blood vessel parameters using a plurality of pieces blood vessel information. However, instead of using a plurality of pieces of blood vessel information, blood vessel information and information regarding the observation target other than the blood vessel information may be used to calculate blood vessel parameters. The information regarding the observation target other than the blood vessel information is, for example, information regarding a part of the observation target (esophagus, stomach, colon, and the like), patient information (age, gender, medical history, and the like), and the state of the mucosal surface (presence or absence of protuberance or the size of protuberance, pit pattern, tone, and the like). For example, in the case of calculating a blood vessel parameter by combining blood vessel information and information regarding a part of the observation target, a parameter set for calculation is prepared in advance for each part of the observation target, and the blood vessel parameter is calculated using the blood vessel information and the parameter set.

Figure 19:
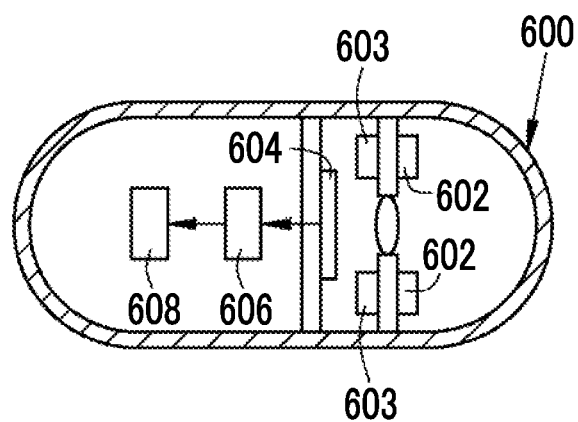
FIG. 19 is a schematic diagram of a capsule endoscope.

In the first to third embodiments described above, the present invention is implemented by the endoscope system 10 (or the endoscope system 310) that performs observation by inserting the endoscope 12, in which the imaging sensor 48 is provided, into the subject. However, the present invention is also suitable for a capsule endoscope system. For example, as shown in FIG. 19, a capsule endoscope system includes at least a capsule endoscope 600 and a processor device (not shown). The capsule endoscope 600 includes a light source 602, a light source control unit 603, an imaging sensor 604, an image signal acquisition processing unit 606, and a transmitting and receiving antenna 608. The light source 602 is configured similarly to the light source 20 of the endoscope system 10, and emits illumination light under the control of the light source control unit 603. The image signal acquisition processing unit 606 functions as the image signal acquisition unit 53, the DSP 56, the noise reduction unit 58, and the signal processing unit 62. The processor device of the capsule endoscope system is configured similarly to the processor device 16 of the endoscope system 310, and also functions as the image processing apparatus 65.

EXPLANATION OF REFERENCES

10: endoscope system
12: endoscope
12a: insertion part
12b: operation unit
12c: bending portion
12d: distal end portion
12e: angle knob
13a: still image acquisition instruction unit
13b: zoom operation unit
14: light source device
16: processor device
18: monitor
19: console
20: light source
22: light source control unit
30a: illumination optical system
30b: imaging optical system
41: light guide
45: illumination lens
46: objective lens
47: zoom lens
48: imaging sensor
51: CDS/AGC circuit
52: A/D converter
53: image signal acquisition unit
56: DSP
58: noise reduction unit
61: memory
62: signal processing unit
63: video signal generation unit
64: storage
65: image processing apparatus
71: first endoscope image
72: second endoscope image
73: shape of mucosal surface
74: surface layer blood vessel
75: middle deep layer blood vessel
91: image acquisition unit
92: blood vessel extraction unit
93: blood vessel information calculation unit
94: blood vessel parameter calculation unit
95: display control unit
97: input device
98: monitor
99: weighting coefficient table
101: difference image
102: difference image
115: endoscope image display portion
121: region of interest
131: setting portion
132: pull-down button
141: blood vessel parameter setting portion
142: pull-down button
143: blood vessel parameter display portion
144a: first blood vessel parameter setting portion
144b: second blood vessel parameter setting portion
145a: first blood vessel parameter display portion 145b: second blood vessel parameter display portion
146a: blood vessel parameter display portion
146b: blood vessel parameter display portion
161: graph
203: determination unit
208: determination result
217: determination result display portion
218: change width
219: graph
220: value of blood vessel parameter
310: endoscope system
600: capsule endoscope
602: light source
603: light source control unit
604: imaging sensor
606: image signal acquisition processing unit
608: transmitting and receiving antenna
PA: blood vessel parameter
PA1: blood vessel parameter
PB: blood vessel parameter
PB2: blood vessel parameter
Ri: inside of region of interest
Ro: region other than region of interest
TH1: first threshold value
TH2: second threshold value

What is claimed is:

1. An image processing apparatus, comprising a processor configured to function as:
   an image acquisition unit that acquires an endoscope image obtained by imaging an observation target with an endoscope;
   a blood vessel extraction unit that extracts a blood vessel for each depth at a specific depth of the observation target from the endoscope image;
   a blood vessel information calculation unit that calculates blood vessel information for each depth regarding the blood vessel extracted by the blood vessel extraction unit; and
   a blood vessel parameter calculation unit that calculates a blood vessel parameter for each depth, which is relevant to the blood vessel at the specific depth, by calculation for each depth using the blood vessel information.

2. The image processing apparatus according to claim 1, wherein the blood vessel information is the number of blood vessels extracted by the blood vessel extraction unit, a thickness, a change in thickness, complexity of thickness change, a length, a change in length, the number of branches, a branching angle, a distance between branch points, the number of crossings, a depth, a height difference, an inclination, an area, a density, an interval, a contrast, a color, a color change, a degree of meandering, blood concentration, oxygen saturation, a proportion of arteries, a proportion of veins, concentration of administered coloring agent, a running pattern, or a blood flow rate.

3. The image processing apparatus according to claim 1, wherein the blood vessel parameter calculation unit calculates the blood vessel parameter of the specific depth using the blood vessel information calculated for the blood vessel at the specific depth.

4. The image processing apparatus according to claim 1, wherein the blood vessel parameter calculation unit calculates the blood vessel parameter of the specific depth using the blood vessel information calculated for blood vessels having depths other than the specific depth.

5. The image processing apparatus according to claim 1, wherein the blood vessel parameter calculation unit calculates the blood vessel parameter by weighting a plurality of pieces of the blood vessel information.

6. The image processing apparatus according to claim 5, wherein the blood vessel parameter calculation unit performs the weighting using a coefficient determined by machine learning.

7. The image processing apparatus according to claim 1, wherein the blood vessel information calculation unit calculates a statistic in a region of interest, which is set in a part or entirety of the endoscope image, as the blood vessel information.

8. The image processing apparatus according to claim 7, wherein the statistic is a maximum value, a minimum value, an average value, a median, or a mode.

9. The image processing apparatus according to claim 7, wherein, in a case of setting the region of interest in a part of the endoscope image, the blood vessel information calculation unit calculates the blood vessel information of the region of interest and also calculates the blood vessel information for a region other than the region of interest, and
   the blood vessel parameter calculation unit calculates the blood vessel parameter using the blood vessel information of the region of interest and the blood vessel information of the region other than the region of interest.

10. The image processing apparatus according to claim 1, the processor being configured to further function as:
    a determination unit that determines a state of a mucous membrane of the observation target using the blood vessel parameter.

11. The image processing apparatus according to claim 10,
    wherein the determination unit determines the state of the mucous membrane of the observation target according to a change of the blood vessel parameter with respect to a depth.

12. The image processing apparatus according to claim 10,
    wherein the determination unit determines the state of the mucous membrane of the observation target using a plurality of the blood vessel parameters.

13. The image processing apparatus according to claim 10,
    wherein the determination unit determines the state of the mucous membrane of the observation target to be one of three or more kinds of states including normal, adenoma, and cancer using the blood vessel parameter.

14. The image processing apparatus according to claim 13,
    wherein the determination unit determines the state of the mucous membrane of the observation target to be one of normal, hyperplastic polyp, SSA/P, adenoma, laterally spreading tumor, and cancer using the blood vessel parameter.

15. The image processing apparatus according to claim 10,
    wherein the determination unit determines a stage of cancer using the blood vessel information or the blood vessel parameter in a case where the state of the mucous membrane of the observation target is cancer.

16. An endoscope system, comprising:
    an endoscope that images an observation target; and
    an image processing apparatus having an image acquisition unit that acquires an endoscope image obtained by imaging the observation target with the endoscope, a blood vessel extraction unit that extracts a blood vessel for each depth at a specific depth of the observation target from the endoscope image, a blood vessel information calculation unit that calculates blood vessel information for each depth regarding the blood vessel extracted by the blood vessel extraction unit, and a blood vessel parameter calculation unit that calculates a blood vessel parameter for each depth, which is relevant to the blood vessel at the specific depth, by calculation for each depth using the blood vessel information.

17. An image processing method, comprising:
a step in which an image acquisition unit acquires an endoscope image obtained by imaging an observation target with an endoscope;
a step in which a blood vessel extraction unit extracts a blood vessel for each depth at a specific depth of the observation target from the endoscope image;
a step in which a blood vessel information calculation unit calculates blood vessel information for each depth regarding the blood vessel extracted by the blood vessel extraction unit; and
a step in which a blood vessel parameter calculation unit calculates a blood vessel parameter for each depth, which is relevant to the blood vessel at the specific depth, by calculation for each depth using the blood vessel information.

* * * * *

UNITED STATES PATENT AND TRADEMARK OFFICE
CERTIFICATE OF CORRECTION

| | |
|---|---|
| PATENT NO. | : 10,426,318 B2 |
| APPLICATION NO. | : 15/936475 |
| DATED | : October 1, 2019 |
| INVENTOR(S) | : Shumpei Kamon |

It is certified that error appears in the above-identified patent and that said Letters Patent is hereby corrected as shown below:

On the Title Page

Item (73) Assignee should read: FUJIFILM Corporation, Tokyo (JP)

Signed and Sealed this
Twenty-sixth Day of November, 2019

Andrei Iancu
*Director of the United States Patent and Trademark Office*